(12) United States Patent
Allison

(10) Patent No.: US 8,275,442 B2
(45) Date of Patent: Sep. 25, 2012

(54) TREATMENT PLANNING SYSTEMS AND METHODS FOR BODY CONTOURING APPLICATIONS

(75) Inventor: John W. Allison, Los Altos, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 203 days.

(21) Appl. No.: 12/565,613

(22) Filed: Sep. 23, 2009

(65) Prior Publication Data

US 2010/0081971 A1      Apr. 1, 2010

Related U.S. Application Data

(60) Provisional application No. 61/100,248, filed on Sep. 25, 2008.

(51) Int. Cl.
*A61B 5/05* (2006.01)
(52) U.S. Cl. ........ 600/407; 600/410; 600/411; 600/416; 600/426; 600/427; 600/436; 600/437; 600/439; 606/27; 606/32; 606/34; 606/41
(58) Field of Classification Search .................. 600/407, 600/410, 411, 416, 425, 427, 436, 437, 439; 606/27, 32, 34, 41; 604/542
See application file for complete search history.

(56) References Cited

U.S. PATENT DOCUMENTS

| | | | |
|---|---|---|---|
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,703,897 A | 11/1972 | Mack et al. |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,140,130 A | 2/1979 | Storm, III |

(Continued)

FOREIGN PATENT DOCUMENTS

CN     1817990 A     8/2006

(Continued)

OTHER PUBLICATIONS

U.S. Appl. No. 12/196,246, filed Aug. 21, 2008, Levinson.

(Continued)

*Primary Examiner* — James Kish
(74) *Attorney, Agent, or Firm* — Perkins Coie LLP

(57) ABSTRACT

Methods and system for treatment planning for non- and minimally-invasive alteration of body adipose tissue for reduction and contouring of body fat are described herein. Treatment plans can be generated by capturing current body part data (e.g., positioning, contour/shape, thickness of adipose tissue, etc.), determining desired outcome of treatment (e.g., percent reduction of adipose tissue thickness, degree of contour change, etc.), and determining treatment parameters to achieve desired results. Algorithms can be used to determine best-fit treatment parameters to use in treatment sessions. In some embodiments, the system can provide a predictive end-result image for communication to patient and/or for determining alteration of desired outcome. In various embodiments, real-time monitoring of feedback data can be used to determine treatment plan efficacy. Additional algorithms can provide real-time comparison of feedback data to anticipated feedback data, and can be used to change treatment parameters in real-time to achieve desired effects.

46 Claims, 15 Drawing Sheets

U.S. PATENT DOCUMENTS

| | | |
|---|---|---|
| 4,202,336 A | 5/1980 | van Gerven et al. |
| 4,266,043 A | 5/1981 | Fujii et al. |
| 4,381,009 A | 4/1983 | Del Bon et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,802,475 A | 2/1989 | Weshahy et al. |
| 4,832,022 A | 5/1989 | Tjulkov et al. |
| 4,846,176 A | 7/1989 | Golden |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A * | 11/1993 | Windhab et al. ............... 426/519 |
| 5,277,030 A | 1/1994 | Miller |
| 5,314,423 A | 5/1994 | Seney |
| 5,330,745 A | 7/1994 | McDow |
| 5,336,616 A | 8/1994 | Livesey et al. |
| 5,339,541 A | 8/1994 | Owens |
| 5,351,677 A | 10/1994 | Kami et al. |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,769,879 A | 6/1998 | Richards et al. |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Gonçalves et al. |
| 5,919,219 A | 7/1999 | Knowlton |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,438,424 B1 | 8/2002 | Knowlton |
| 6,438,964 B1 | 8/2002 | Giblin |
| 6,453,202 B1 | 9/2002 | Knowlton |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,699,266 B2 | 3/2004 | Lachenbruch et al. |
| 6,718,785 B2 | 4/2004 | Bieberich |
| 6,746,474 B2 | 6/2004 | Saadat |
| 6,749,624 B2 | 6/2004 | Knowlton |
| 6,764,502 B2 | 7/2004 | Bieberich |
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,022,121 B2 | 4/2006 | Stern et al. |
| 7,037,326 B2 | 5/2006 | Lee et al. |
| 7,077,858 B2 | 7/2006 | Fletcher et al. |
| 7,081,111 B2 | 7/2006 | Svaasand et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,183,360 B2 | 2/2007 | Daniel et al. |

| | | | |
|---|---|---|---|
| 7,189,252 B2 | 3/2007 | Krueger | |
| 7,192,426 B2 | 3/2007 | Baust et al. | |
| 7,204,832 B2 | 4/2007 | Altshuler et al. | |
| 7,220,778 B2 | 5/2007 | Anderson et al. | |
| 7,367,341 B2 | 5/2008 | Anderson et al. | |
| 2002/0049483 A1 | 4/2002 | Knowlton | |
| 2002/0058975 A1 | 5/2002 | Bieberich | |
| 2002/0062142 A1 | 5/2002 | Knowlton | |
| 2002/0117293 A1 | 8/2002 | Campbell | |
| 2002/0151887 A1 | 10/2002 | Stern et al. | |
| 2002/0188286 A1 | 12/2002 | Quijano et al. | |
| 2003/0069618 A1 | 4/2003 | Smith et al. | |
| 2003/0079488 A1 | 5/2003 | Bieberich | |
| 2003/0100936 A1 | 5/2003 | Altshuler et al. | |
| 2003/0109908 A1 | 6/2003 | Lachenbruch et al. | |
| 2003/0109910 A1 | 6/2003 | Lachenbruch et al. | |
| 2003/0125649 A1 | 7/2003 | McIntosh et al. | |
| 2003/0199226 A1 | 10/2003 | Sommer et al. | |
| 2003/0220674 A1* | 11/2003 | Anderson et al. | 607/96 |
| 2003/0236487 A1 | 12/2003 | Knowlton | |
| 2004/0006328 A1 | 1/2004 | Anderson | |
| 2004/0030332 A1 | 2/2004 | Knowlton et al. | |
| 2004/0039312 A1 | 2/2004 | Hillstead et al. | |
| 2004/0049178 A1 | 3/2004 | Abboud et al. | |
| 2004/0073079 A1 | 4/2004 | Altshuler et al. | |
| 2004/0074629 A1 | 4/2004 | Noel | |
| 2004/0093042 A1 | 5/2004 | Altshuler et al. | |
| 2004/0104012 A1 | 6/2004 | Zhou et al. | |
| 2004/0162596 A1 | 8/2004 | Altshuler et al. | |
| 2004/0199226 A1 | 10/2004 | Shadduck | |
| 2004/0210214 A1 | 10/2004 | Knowlton | |
| 2004/0210287 A1 | 10/2004 | Greene | |
| 2004/0259855 A1 | 12/2004 | Anderson et al. | |
| 2005/0049661 A1 | 3/2005 | Koffroth | |
| 2005/0154431 A1 | 7/2005 | Quistgaard et al. | |
| 2005/0159986 A1* | 7/2005 | Breeland et al. | 705/3 |
| 2005/0182462 A1 | 8/2005 | Chornenky et al. | |
| 2005/0222565 A1 | 10/2005 | Manstein | |
| 2005/0251120 A1 | 11/2005 | Anderson et al. | |
| 2006/0030778 A1 | 2/2006 | Mendlein et al. | |
| 2006/0036300 A1 | 2/2006 | Kreindel | |
| 2006/0074313 A1* | 4/2006 | Slayton et al. | 600/439 |
| 2006/0079852 A1 | 4/2006 | Bubb et al. | |
| 2006/0122509 A1 | 6/2006 | Desilets | |
| 2006/0200063 A1 | 9/2006 | Munro et al. | |
| 2006/0234899 A1 | 10/2006 | Nekmard et al. | |
| 2006/0270745 A1 | 11/2006 | Hunt et al. | |
| 2007/0010861 A1 | 1/2007 | Anderson et al. | |
| 2007/0032561 A1 | 2/2007 | Lin et al. | |
| 2007/0141265 A1 | 6/2007 | Thomson | |
| 2007/0198071 A1 | 8/2007 | Ting et al. | |
| 2007/0239075 A1* | 10/2007 | Rosenberg et al. | 601/2 |
| 2007/0249519 A1* | 10/2007 | Guha et al. | 514/2 |
| 2007/0255362 A1 | 11/2007 | Levinson et al. | |
| 2007/0270925 A1 | 11/2007 | Levinson | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0140371 A1* | 6/2008 | Warner | 703/11 |
| 2008/0287839 A1 | 11/2008 | Rosen et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0118722 A1 | 5/2009 | Ebbers et al. | |

FOREIGN PATENT DOCUMENTS

| | | |
|---|---|---|
| DE | 532976 C | 9/1931 |
| DE | 2851602 | 6/1980 |
| DE | 4213584 A1 | 11/1992 |
| DE | 4224595 | 1/1994 |
| EP | 0263069 A2 | 4/1988 |
| EP | 0397043 | 11/1990 |
| EP | 0406244 A1 | 1/1991 |
| EP | 0598824 A1 | 6/1994 |
| GB | 2286660 A | 8/1995 |
| GB | 2323659 A | 9/1998 |
| JP | 63076895 A | 4/1988 |
| JP | 3259975 A | 11/1991 |
| JP | 4093597 A | 3/1992 |
| JP | 7268274 A | 10/1995 |
| JP | 09164163 A | 6/1997 |
| JP | 10216169 A | 8/1998 |
| JP | 2005520608 T | 7/2005 |
| JP | 2006026001 A | 2/2006 |
| KR | 1020040094508 | 11/2004 |
| SU | 532976 A1 | 11/1978 |
| TW | 0476644 | 2/2002 |
| WO | WO-9636293 A1 | 11/1996 |
| WO | WO-9637158 A1 | 11/1996 |
| WO | WO-9705828 A1 | 2/1997 |
| WO | WO-9722262 A2 | 6/1997 |
| WO | WO-9841157 A1 | 9/1998 |
| WO | WO-9938469 A1 | 8/1999 |
| WO | WO-0044346 A1 | 8/2000 |
| WO | WO-0205736 A2 | 1/2002 |
| WO | WO-02102921 A1 | 12/2002 |
| WO | WO-03078596 A2 | 9/2003 |
| WO | WO-04000098 A2 | 12/2003 |
| WO | WO-2004080279 A2 | 9/2004 |
| WO | WO-2005046540 A1 | 5/2005 |
| WO | WO-2006066226 A1 | 6/2006 |
| WO | WO-2006127467 A2 | 11/2006 |
| WO | WO-2007041642 A2 | 4/2007 |

OTHER PUBLICATIONS

U.S. Appl. No. 12/275,002, filed Nov. 20, 2008, Martens.
U.S. Appl. No. 12/275,014, filed Nov. 20, 2008, Martens.
U.S. Appl. No. 12/337,544, filed Dec. 17, 2008, Alison.
Ardevol, "Cooling rates of tissue samples during freezing with liquid nitrogen," J. of Biochem and Biophysical Methods, 27, 77-86 (1993).
Bohm et al., "Saline-enhanced radiofrequency ablation of breast tissue: an in vitro feasibility study," Invest Radiol, 2000, pp. 149-157, vol. 35—issue (3).
Bondei, E. et al., "Disorders of Subcutaneous Tissue (Cold Panniculitis)," Dermatology in General Medicine, Chapter 108, Section 16: 1333-1334, 1993.
Burge, S.M. et al., "Hair Follicle Destruction and Regeneration in Guinea Pig Skin after Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Disclosure re: "Method and Apparatus for Regional Fat Reduction Using Controlled and Sustained Cooling of Skin Surface".
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.
Epstein, E.H. et al., "Popsicle Panniculitis," The New England Journal of Medicine, 282(17):996-67, 1970.
Gage, "Current Progress in Cryosurgery," Cryobiology 25, 483-486 (1988).
Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2005/045988; Applicant: The General Hospital Corporation; Mailed on Apr. 25, 2006, 14 pages.

International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/062508; Applicant: Juniper Medical, Inc.; Date of Mailing: Jul. 20, 2007, 13 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2009/058088; Applicant: Zeltiq Aesthetics, Inc.; Date of Mailing: Nov. 20, 2009, 14 pages.
International Search Report for EP07758558.6; Applicant: Zeltiq Aesthetics, Inc.; Mailed on Jul. 20, 2007, 4 pages.
Kellum, R.E. et al., "Sclerema Neonatorum: Report of Case and Analysis of Subcutaneous and Epidermal-Dermal Lipids by Chromatographic Methods," Arch. Derm., 97:372-380, 1968.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Moschella, S.L. et al., "Diseases of the Subcutaneous Tissue," Derm., Section 2:1169-1181, 1985.

Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis—a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 11/359,092; Mailed on Nov. 19, 2009, 13 pages.
Non-Final Office Action; U.S. Appl. No. 11/435,502; Date of Mailing: Jul. 17, 2009, 10 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2:59-71.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells, " J. Tiss. Cult. Meth., 14:85-92, 1992.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
International Search Report and Written Opinion for PCT/US2009/067973; Applicant: Zeltiq Aesthetics, Inc.; Date of Mailing: Feb. 18, 2010, 10 pages.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 10/391,221; Date of Mailing: Jul. 22, 2005, 6 pages.
Non-Final Office Action; U.S. Appl. No. 11/016,196; Date of Mailing: Apr. 22, 2008, 11 pages.
Non-Final Office Action; U.S. Appl. No. 11/016,196; Date of Mailing: Sep. 25, 2009, 8 pages.
Non-Final Office Action; U.S. Appl. No. 11/528,225; Date of Mailing: Apr. 12, 2010, 11 pages.
Pre-Interview Office Action; U.S. Appl. No. 11/434,478; Date of Mailing: May 6, 2010, 4 pages.

* cited by examiner

700

702

TREATMENT PLAN

Practitioner ID No.  123456-789

704 { Patient

| Name ▼ | Mary T. Smith |

Name
Medical ID No.

706 { ● New Patient
○ Existing Patient

708
| ENTER | CANCEL |

TREATMENT PLAN: NEW PATIENT INFORMATION

Insurance ● YES            GENDER ● MALE
○ NO                     ○ FEMALE

Plan No. ABC-123           AGE   44  (years)

712 { Medical Conditions        HEIGHT  66  (inches)
None

WEIGHT  156  (pounds)

Prescription Medications
None

714
| ENTER | CANCEL |

TREATMENT PLAN
Session No.: 10987654
718

TARGET REGION STATUS

722

| Abdomen ▼ |
| Love Handle |
| Abdomen |
| Back |
| Thigh |

Surface Area (mm2)  2.1 x 10⁴

Thickness (mm)  32

Uniform Thickness?  ● YES
○ NO

720

724

Image File Upload
File Name:
726

[BROWSE]  728  [ENTER]  [CANCEL]

TREATMENT PLAN
Session No.: 10987654
718

TREATMENT OBJECTIVE

Adipose Tissue Reduction?  ● YES
○ NO

Amount of Reduction:  [ ] %
or
[ ] mm

732

734

[ENTER]  [CANCEL]

*FIG. 7D*

| | | | |
|---|---|---|---|
| PATIENT | GENDER | FEMALE | YES |
| PATIENT | GENDER | MALE | NULL |
| PATIENT | AGE | 20-39 | NULL |
| PATIENT | AGE | 40-54 | YES |
| PATIENT | AGE | 55-70 | NULL |
| STATUS | TARGET REGION | LOVE HANDLE | NULL |
| STATUS | TARGET REGION | ABDOMEN | YES |
| STATUS | TARGET REGION | BACK | NULL |
| STATUS | TARGET REGION | THIGH | NULL |
| STATUS | THICKNESS | 4-20 mm | NULL |
| STATUS | THICKNESS | 20-40 mm | YES |
| STATUS | THICKNESS | +40 mm | NULL |
| STATUS | THICKNESS | UNIFORM | YES |
| STATUS | THICKNESS | NON-UNIFORM | NULL |
| OBJECTIVE | REDUCTION | 1-5 % | NULL |
| OBJECTIVE | REDUCTION | 5-10 % | YES |
| OBJECTIVE | REDUCTION | 10-15 % | NULL |
| OBJECTIVE | REDUCTION | 15-20 % | NULL |
| ⋮ | ⋮ | ⋮ | ⋮ |

910   920   930   940

900

*FIG. 9*

TREATMENT PLANNING SYSTEMS AND METHODS FOR BODY CONTOURING APPLICATIONS

CROSS-REFERENCE TO APPLICATION(S) INCORPORATED BY REFERENCE

The present application claims priority to U.S. Provisional Patent Application No. 61/100,248 filed Sep. 25, 2008, entitled "TREATMENT PLANNING SYSTEMS AND METHODS FOR BODY CONTOURING APPLICATIONS," and incorporated herein in its entirety by reference.

The present application incorporates the following commonly-assigned U.S. Patent Applications herein by reference in their entirety:

U.S. patent application Ser. No. 11/750,953, filed on May 18, 2007 (Publication No. 2008/0287839), entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2007/0198071, now U.S. Pat. No. 7,854,754, entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. patent application Ser. No. 11/933,066, filed Oct. 31, 2007 (Publication No. 2009/0118722), entitled "METHOD AND APPARATUS FOR COOLING SUBCUTANEOUS LIPID-RICH CELLS OR TISSUE";

U.S. patent application Ser. No. 11/777,995, filed Jul. 13, 2007(Publication No. 2009/0018624), entitled "LIMITING USE OF DISPOSABLE PATIENT PROTECTION DEVICES";

U.S. patent application Ser. No. 11/777,992, filed Jul. 13, 2007 (Publication No. 2009/0018623), entitled "SYSTEM FOR TREATING LIPID-RICH REGIONS";

U.S. patent application Ser. No. 11/777,999, filed Jul. 13, 2007 (Publication No. 2009/0018625), entitled "MANAGING SYSTEM TEMPERATURE TO REMOVE HEAT FROM LIPID-RICH REGIONS";

U.S. patent application Ser. No. 11/778,003, filed Jul. 13, 2007 (Publication No. 2009/0018627), entitled "SECURE SYSTEM FOR REMOVING HEAT FROM LIPID-RICH REGIONS";

U.S. patent application Ser. No. 11/778,001 (Publication No. 2009/0018626), entitled "USER INTERFACES FOR A SYSTEM THAT REMOVES HEAT FROM LIPID-RICH REGIONS," filed Jul. 13, 2007;

U.S. Patent Publication No. 2008/0077202, now U.S. Pat. No. 8,192,474, entitled "TISSUE TREATMENT METHODS"; and U.S. patent application Ser. No. 12/337,544 (Publication No. 2010/0152824), entitled "SYSTEMS AND METHODS WITH INTERRUPT/RESUME CAPABILITIES FOR COOLING SUBCUTANEOUS LIPID-RICH CELLS," filed Dec. 17, 2008.

TECHNICAL FIELD

The present application relates generally to treatment planning systems and methods including systems and methods for generating and implementing treatment plans for body contouring applications and other non-invasive medical applications.

BACKGROUND

Excess body fat, or adipose tissue, may be present in various locations of the body, including, for example, the thigh, buttocks, abdomen, knees, back, face, arms, chin, and other areas. Excess adipose tissue can detract from personal appearance and athletic performance. Moreover, excess adipose tissue is thought to magnify the unattractive appearance of cellulite, which forms when subcutaneous fat lobules protrude and penetrate into the dermis and create dimples where the skin is attached to underlying structural fibrous strands. Cellulite and excessive amounts of adipose tissue are often considered to be unappealing. Moreover, significant health risks may be associated with higher amounts of excess body fat.

Adipose tissue is subdivided into lobules by connective collagen tissue called fibrous septae. The fibrous septae, which are generally oriented perpendicular to the skin surface and anchor the epidermis and dermis to the underlying fascia and muscle, are organized within the subcutaneous layer to form a connective web around the adipose cells. Subcutaneous adipose cells are not uniformly distributed throughout the subcutaneous tissue layer (e.g., between the dermis and the muscle layers), but exhibit regional differences in lobule size and shape. These regional differences can, in part, be due to gender, age, genetics and physical conditioning among other physiological factors. The number, size, distribution and orientation of fibrous septae also vary by body location, gender and age. For example, histological studies have shown that fibrous septae architecture in women differs from that in men.

In males, fibrous septae form a network of cris-crossing septa of connective tissue that divide fat-cell chambers into small, polygonal units. In contrast, fibrous septae in females generally tend to be oriented perpendicular to the cutaneous surface, tending to create "fat cell chambers" or "papillae adiposae" that are columnar in shape and sequestered by the connective strands and the overlaying dermis layer. When the fibrous septae are more uniform in size and elasticity as well as positioned evenly throughout the subcutaneous layer, such as those characteristic of males, tension and stress is distributed evenly among the connective strands and the adipose cells are largely contained within the web of collagen. However, the subcutaneous fat cell chambers characteristic of females can bulge into the dermis, thereby changing the appearance of the skin surface. Added weight (e.g., fat cell lipid volume) may cause enlargement of the fat lobules, which can then further protrude into the dermis. Nürnberger, F., Müller, G., "So-Called Cellulite: An Invented Disease" *J. Dermatol. Surg. Oncol.* 4:3, 221-229 (1978).

Cellulite (Gynoid lipodystrophy) is typically a hormonally mediated condition characterized by the uneven distribution of adipose tissue in the subcutaneous layer that gives rise to an irregular, dimpled skin surface common in women. Cellulite-prone tissue can be characterized by the uneven thickness and distribution of some fibrous septae strands. Thicker strands can continue to act as a buttress to herniation and bulging of the adipose chambers into the dermis; however, thinning strands near the dermal layer permit the adipocytes to bulge into and penetrate the dermal layer, and in some cases cause thinning of the dermal layer. In exacerbated conditions of cellulite, fat lobules are enlarged near the dermal layer with excessive stored lipids and bound only by thin and focally loose connective tissue strands. Piérard, G. E., Nizet, J. L, Piérard-Franchimont, C., "Cellulite: From Standing Fat Herniation to Hypodermal Stretch Marks," *Am. J. Dermatol.* 22:1, 34-37 (2000).

Various non- and minimally invasive treatment modalities have been offered for improving the appearance of cellulite, including cold therapy, the use of heating such as by radio frequency, microwave, or laser energy, the use of focused ultrasound energy, mesotherapy, and other techniques.

A variety of similar and identical methods have been used or offered to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, a high intensity focused ultrasound (HIFU) radiation such as described in U.S. Pat. Nos. 6,071,239, 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al. The entire disclosures of the references listed in this paragraph are incorporated herein by reference.

The process of treating a patient having excess body fat and/or cellulite with one or more of non-invasive and/or minimally invasive techniques can include several preparative and planning stages. For example, a preliminary examination and assessment of the region to be treated is required. This preliminary examination is followed by development of a treatment prescription by a medical professional.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 7A-7D are views of a user interface for interacting with a treatment plan generator in accordance with an embodiment of the disclosure.

FIG. 9 is a schematic block diagram illustrating table data structures employed by the treatment planning system of FIG. 4 in accordance with an embodiment of the disclosure.

DETAILED DESCRIPTION

Figure 1:
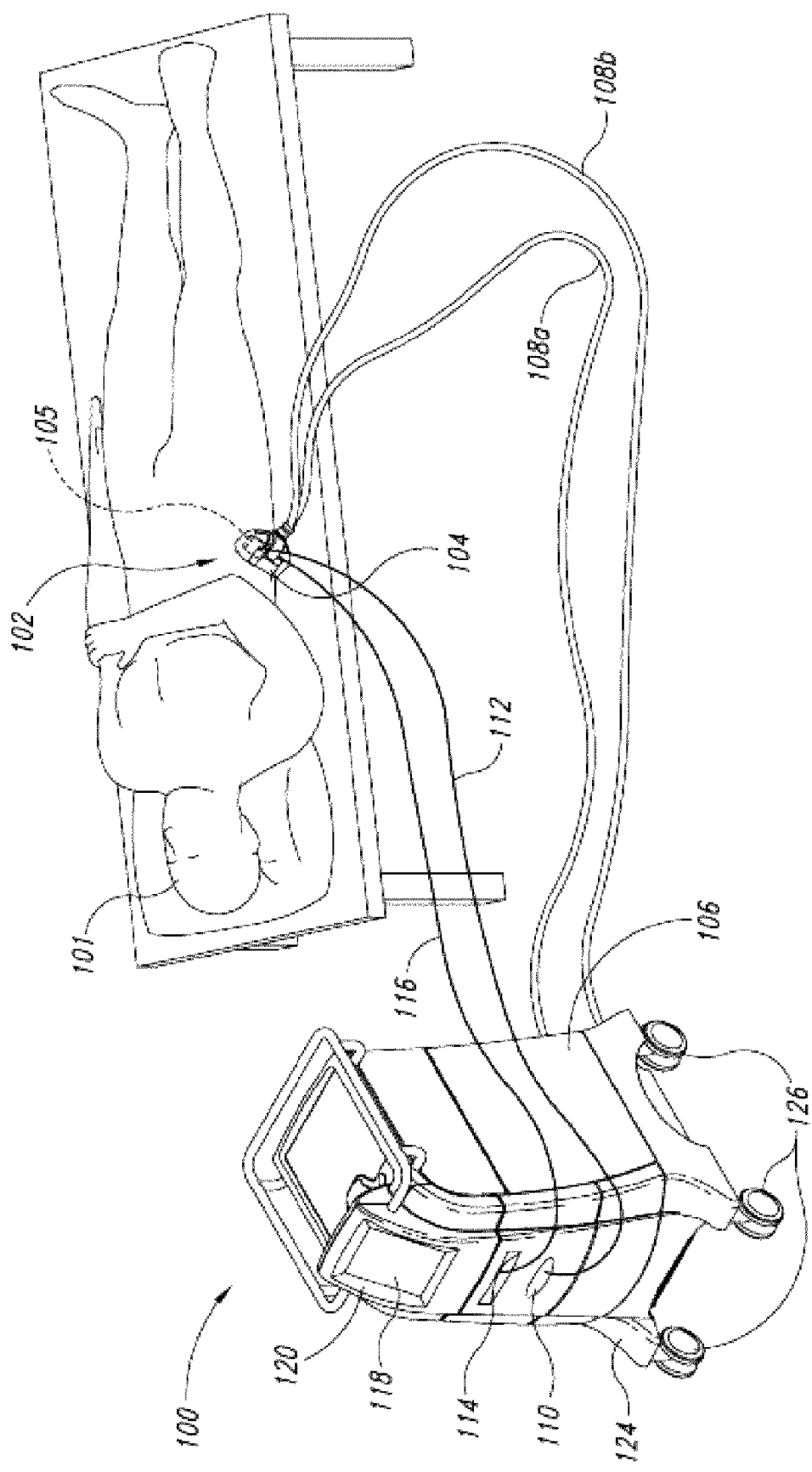
FIG. 1 is an isometric view schematically illustrating a treatment system for treating subcutaneous lipid-rich regions of a patient in accordance with an embodiment of the disclosure.

A. Embodiments of Treatment Planning Systems and Methods

1. System Overview

Systems and methods are provided herein that enable generation and implementation of a medical treatment plan for body contouring applications. In some embodiments, a treatment plan can be automatically generated and provided to medical personnel and/or a patient. In further embodiments, the treatment plan can be automatically implemented, for example, to remove excess body fat, change a body contour by removing adipose tissue, improving the appearance of cellulite (which may or may not include the treatment of adipose tissue), etc. The treatment plan can be based on patient-specific information, patient desired treatment results, a priori information and empirically-derived information relating to previously implemented treatments and treatment results and/or clinically-based treatment modeling.

A treatment planning system is described for providing a recommended treatment strategy for removing excess subcutaneous adipose tissue, such as by cooling. The treatment planning system includes a computing device having a processor, memory and data stored in the memory. In one embodiment, the system can include a computer network for transmitting treatment plan requests and data, images and treatment plans. The treatment planning system can also include a database connected to the computer network for storing a plurality of model data sets and a plurality of treatment parameters. The model data sets can include empirically-derived and a priori information relating to conditions of excess subcutaneous adipose tissue, treatment parameters and options, and treatment results.

The system also includes encoded computing device instructions for planning treatment. The instructions (e.g., logic programming) may be stored in the memory and executable by the processor, or in another embodiment, reside on a server in communication with the computer network. The instructions include logic steps that accept patient-specific data describing the patient's pre-treatment condition, logic steps that accept data relating to a desired post-treatment outcome, and logic steps that evaluate the pre-treatment data and desired post-treatment outcome data relative to the plurality of model data sets. The instructions can further include logic steps that calculate a best-fit combination of treatment parameters from the plurality of treatment parameters to formulate a patient-specific treatment plan.

In further embodiments, the treatment planning system can report alternative treatment plans based on specific criteria. For example, the patient and/or medical personnel may desire to have a treatment plan that separates a proposed treatment session into multiple treatment sessions over a given period of time.

One embodiment of the disclosure is directed to one or more algorithms to assist a medical practitioner in the selection of a treatment plan for reduction and/or contouring of a patient's adipose tissue at a target body region. Generally, the algorithm(s) includes the steps of 1) acquiring pre-treatment data about the patient and the target region; 2) evaluating the pre-treatment data to automatically categorize the patient's target region into one or more pre-determined classification data sets; 3) acquiring selected input data about the desired post-treatment outcome; 4) automatically calculating treatment parameters for treating the target region and for achieving the desired outcome, 5) predictive modeling of the post-treatment outcome; and 5) generating one or more treatment plans.

In some embodiments, the algorithm(s) can include logic steps for optimizing and/or changing the anticipated post-treatment outcome based upon one or more subjective criteria and/or personal preference. In other embodiments, the algorithm(s) can include steps for monitoring, in real-time, treatment system feedback data, comparing the treatment system feedback data to predicted feedback data based upon the predictive modeling of the anticipated post-treatment outcome, and when a difference is detected between actual and predictive feedback, modifying the treatment plan in real-time such that the treatment achieves the anticipated post-treatment outcome.

2. Suitable Treatment Systems

FIG. 1 and the following discussion provide a brief, general description of one example of a suitable treatment system 100 in which aspects of the disclosure can be implemented. Those skilled in the relevant art will appreciate that the disclosure can be practiced with other treatment systems and treatment protocols, including invasive, minimally invasive, other non-invasive medical treatment systems, and/or combinations of one or more of the above for treating a patient. In general, the term "treatment system", as used generally herein, refers to any of the above system categories of medical treatment as well as any treatment regimes or medical device usage.

In one embodiment, the treatment system 100 is suitable for treating a subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. When cooling subcutaneous tissues to a temperature lower than 37° C., subcutaneous lipid-rich cells can selectively be affected. In general, the epidermis and dermis of the patient 101 have lower amounts of unsaturated fatty acids compared to the underlying lipid-rich cells forming the subcutaneous tissues. Because non-lipid-rich cells usually can withstand colder temperatures better than lipid-rich cells, the subcutaneous lipid-rich cells can selectively be affected while maintaining the integrity of the non-lipid-rich cells in the dermis, epidermis and other surrounding tissue. In some embodiments, the treatment system 100 can apply cooling temperatures to the skin of the patient in a range of from about −20° C. to about 20° C. In other embodiments, the cooling temperatures can be from about −20° C. to about 10° C., from about 0° C. to about 20° C., from about −15° C. to about 5° C., from about −5° C. to about 15° C., or from about −10° C. to about 0° C.

Without being bound by theory, the selective effect of cooling on lipid-rich cells is believed to result in, for example, membrane disruption, shrinkage, disabling, destroying, removing, killing, or another method of lipid-rich cell alteration. Such alteration is believed to be an intermediate and/or final result of one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451(1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response. Temperature exposures that elicit these apoptotic events in lipid-rich cells may contribute to long-lasting and/or permanent reduction and reshaping of subcutaneous adipose tissue.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews*, 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999). In various embodiments, the system 100 includes a controller, a computing device, a data acquisition device, a treatment unit, and one or more applicators. The system can employ these components in various embodiments to receive a selection of a treatment profile and apply the selected treatment using an applicator.

FIG. 1 is an isometric view schematically illustrating a treatment system 100 for non-invasively removing heat from subcutaneous lipid-rich regions of a subject patient 101 in accordance with an embodiment of the disclosure. The system 100 can include a treatment device 104 including an applicator 105 that engages a target region of the subject 101. The treatment device 104 can be placed, for example, at an abdominal area 102 of the subject 101 or another suitable area for cooling or removing heat from the subcutaneous lipid-rich cells of the subject 101. It will be understood that treatment devices 104 and applicators 105 can be provided having various configurations, shapes and sizes suitable for different body regions and body parts such that any suitable area for removing heat from a subcutaneous lipid-rich region of the subject 101 can be achieved.

An applicator, such as applicator 105, is a component of the system 100 that cools a region of a subject 101, such as a human or animal (i.e., "patient"). Various types of applicators may be applied during treatment, such as a vacuum applicator, a belt applicator (either of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators and their configurations usable, or adaptable for use, with system 100 variously are described in, e.g., commonly assigned U.S. Patent Publication Nos. 2007/0198071, 2008/0077201, and 2008/0077211 and in U.S. patent application Ser. No. 11/750,953. In further embodiments, the system 100 may also include a patient protection device (not shown) incorporated into or configured for use with the applicator that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

In the present example, the system 100 can further include a treatment unit 106 and supply and return fluid lines 108*a-b* between the treatment device 104 and the treatment unit 106. A treatment unit 106 is a device that, based on variable power input, can increase or decrease the temperature at a connected treatment device 104 that in turn may be attached to or incorporated into the applicator 105. The treatment unit 106 can remove heat from a circulating coolant to a heat sink and provide a chilled coolant to the treatment device 104 via the fluid lines 108*a-b*. Alternatively, treatment unit 106 can circulate warm coolant to the treatment device 104 during periods of warming. Examples of the circulating coolant include water, glycol, synthetic heat transfer fluid, oil, a refrigerant, and/or any other suitable heat conducting fluid. The fluid lines 108*a-b* can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. Alternatively, a municipal water supply (e.g., tap water) can be used in place of the treatment unit 106. One skilled in the art will recognize that there are a number of other cooling technologies that could be used such that the treatment unit or chiller need not be limited to those described herein.

In this example, the treatment device 104 includes at least one applicator 105 and is associated with at least one treatment unit 106. The applicator 105 can provide mechanical energy to create a vibratory, massage, and/or pulsatile effect. The applicator 105 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy or other mechanical energy to the treatment site. Further examples include a plurality of actuators for use in connection with a single treatment device 104 and/or applicator 105 in any desired combination. For example, an eccentric weight actuator can be associated with one treatment device 104 or applicator 105, while a pneumatic motor can be associated with another section of the same treatment device or applicator. This, for example, would give the operator of the treatment system 100 options for differential treatment of lipid rich cells within a single region or among multiple regions of the subject 101. The use of one or more actuators and actuator types in various combinations and configurations with a treatment device 104 or applicator 105 may be possible.

The treatment device 104 can include one or more heat exchanging units. The heat exchanging unit can be a Peltier-type thermoelectric element, and the treatment device 104 can have multiple individually controlled heat exchanging units (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Treatment devices having multiple individually controlled heat exchanging units are described in commonly assigned U.S. Patent Publication No. 2008/0077211.

The system 100 can further include a power supply 110 and a controller 114 operatively coupled to the treatment device 104 and the applicator 105. In one embodiment, the power supply 110 can provide a direct current voltage to the thermoelectric treatment device 104 and/or the applicator 105 to remove heat from the subject 101. The controller 114 can monitor process parameters via sensors (not shown) placed proximate to the treatment device 104 via a control line 116 to, among other things, adjust the heat removal rate based on the process parameters. The controller 114 can further monitor process parameters to adjust the applicator 105 based on treatment parameters, such as treatment parameters defined in a custom treatment profile or patient-specific treatment plan.

The controller 114 can exchange data with the applicator 105 via an electrical line 112 or, alternatively, via a wireless or an optical communication link. Note that control line 116 and electrical line 112 are shown in FIG. 1 without any support structure. Alternatively, control line 116 and electrical line 112 (and other lines including, but not limited to fluid lines 108a-b) may be bundled into or otherwise accompanied by a conduit or the like to protect such lines, enhance ergonomic comfort, minimize unwanted motion (and thus potential inefficient removal of heat from subject 101), and to provide an aesthetic appearance to system 100. Examples of such a conduit include a flexible polymeric, fabric, or composite sheath, an adjustable arm, etc. Such a conduit (not shown) may be designed (via adjustable joints, etc.) to "set" the conduit in place for the treatment of subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, or any other device suitable for accepting user input. The output device 120 can include a display or touch screen, a printer, a medium reader, an audio device, any combination thereof, and any other device or devices suitable for providing user feedback. In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the treatment device 104 and/or applicator 105. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the treatment device 104 and/or the applicator 105 and/or the patient protection device described above. In yet other embodiments, the various components can be fixedly installed at a treatment site. Further details with respect to components and/or operation of treatment device 104, treatment unit 106, applicator 105 and other components may be found in commonly-assigned U.S. patent application Ser. No. 11/750,953.

In operation, and upon receiving input to start a treatment protocol, the controller 114 can cause the applicator 105 to cycle through each segment of a prescribed treatment plan. In so doing, the applicator 105 applies power to one or more treatment devices 104, such as thermoelectric coolers (e.g., TEC "zones"), to begin a cooling cycle and, for example, activate features or modes such as vibration, massage, vacuum, etc. Using temperature sensors (not shown) proximate to the one or more treatment devices 104, the patient's skin, a patient protection device, or other locations or combinations thereof, the controller 114 determines whether a temperature or heat flux is at a sufficient temperature close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the system 100 may attempt to heat or cool the tissue to the target temperature or to provide by a target heat flux, a sensor may measure a sufficiently close temperature. If the target temperature has not been reached, power can be increased or decreased to change heat flux, to maintain the target temperature or "setpoint." When the prescribed segment duration expires, the controller 114 may apply the temperature and duration indicated in the next treatment profile segment. In some embodiments, temperature can be controlled using a variable other than, or in addition to, power.

Although a noninvasive applicator is illustrated and discussed herein, minimally invasive applicators may also be employed. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007-0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004-0215294, entitled "CRYOTHERAPY PROBE"; U.S. Pat. No. 7,083,612, entitled "CRYOTHERAPY SYSTEM"; and U.S. Publication No. 2005-0261753, entitled "METHODS AND SYSTEMS FOR CRYOGENIC COOLING".

3. Suitable Computing Environments

Figure 2:
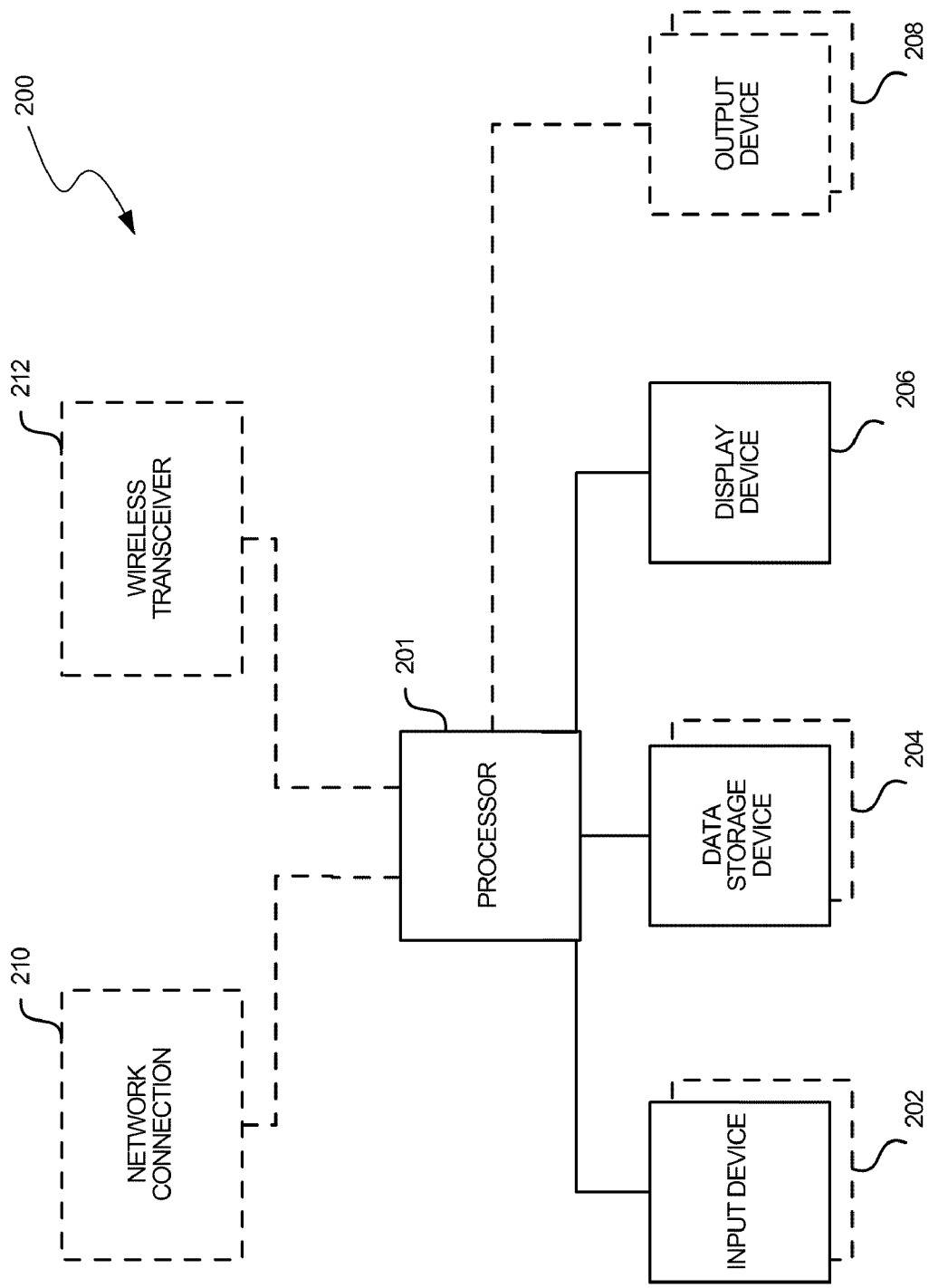
FIG. 2 is a block diagram of a basic and suitable computer that may employ aspects of the disclosure.

FIG. 2 and the following discussion provide a general description of a suitable computing environment in which aspects of the disclosure can be implemented. Although not required, aspects and embodiments of the disclosure will be described in the general context of computer-executable instructions, such as routines executed by a general-purpose computer, e.g., a server or personal computer. Those skilled in the relevant art will appreciate that the disclosure can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The disclosure can be embodied in a special purpose computer or data processor that is specifically programmed, configured or constructed to perform one or more of the computer-executable instructions explained in detail below. Indeed, the term "computer", as used generally herein, refers to any of the above devices, as well as any data processor.

The disclosure can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the disclosure described below may be stored or distributed on computer-readable media, including magnetic and optically readable and removable computer discs, stored as firmware in chips (e.g., EEPROM chips), as well as distributed electronically over the Internet or over other networks (including wireless networks). Those skilled in the relevant art will recognize that portions of the disclosure may reside on a server computer, while corresponding portions reside on a client computer. Data structures and transmission of data particular to aspects of the disclosure are also encompassed within the scope of the disclosure.

Referring to FIG. 2, one embodiment of the disclosure employs a computer 200, such as a personal computer or workstation, having one or more processors 201 coupled to one or more user input devices 202 and data storage devices 204. The computer is also coupled to at least one output device such as a display device 206 and one or more optional additional output devices 208 (e.g., printer, plotter, speakers, tactile or olfactory output devices, etc.). The computer may be coupled to external computers, such as via an optional network connection 210, a wireless transceiver 212, or both.

The input devices 202 may include a keyboard and/or a pointing device such as a mouse. Other input devices are possible such as a microphone, joystick, pen, touch screen, scanner, digital camera, video camera, and the like. Further input devices can include medical imaging devices (e.g., Magnetic Resonance Imaging device, Computed Tomography imaging device, x-ray, ultrasound, surface profile scanning devices, etc.). The data storage devices 204 may include any type of computer-readable media that can store data accessible by the computer 200, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 2).

Figure 3:
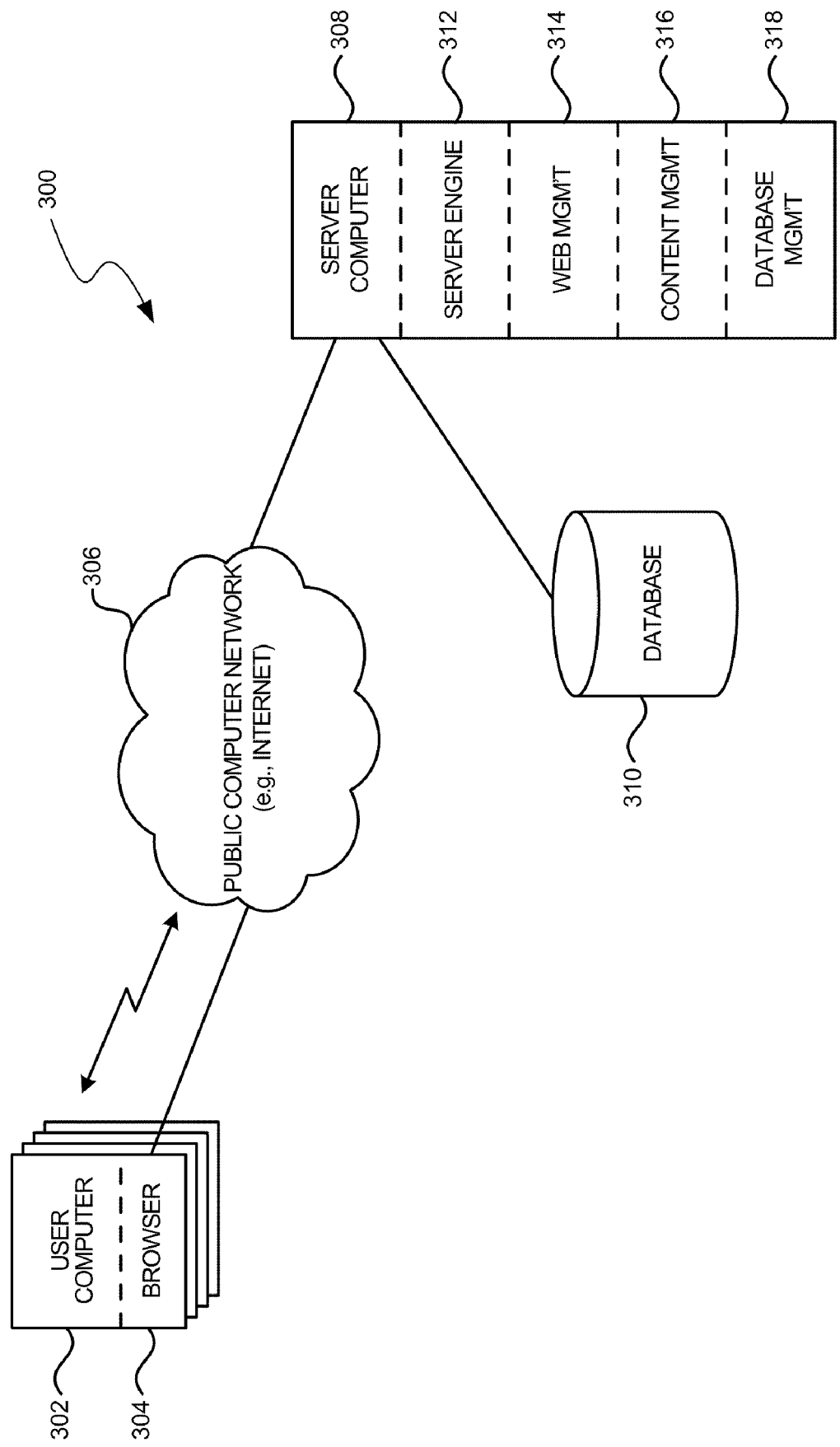
FIG. 3 is a block diagram illustrating a simple, yet suitable system in which aspects of the disclosure may operate in a networked computer environment.

Aspects of the disclosure may be practiced in a variety of other computing environments. For example, referring to FIG. 3, a distributed computing environment with a network interface includes one or more user computers 302 in a system 300 are shown, each of which includes a browser program module 304 that permits the computer to access and exchange data with the Internet 306, including web sites within the World Wide Web portion of the Internet. The user computers may be substantially similar to the computer described above with respect to FIG. 2. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. More importantly, while shown with network browsers, any application program for providing a graphical user interface to users may be employed, as described in detail below; the use of a web browser and web interface are only used as a familiar example here.

At least one server computer 308, coupled to the Internet or World Wide Web ("Web") 306, performs much or all of the functions for receiving, routing and storing of electronic messages, such as web pages, data streams, audio signals, and electronic images. While the Internet is shown, a private network, such as an intranet may indeed be preferred in some applications. The network may have a client-server architecture, in which a computer is dedicated to serving other client computers, or it may have other architectures such as a peer-to-peer, in which one or more computers serve simultaneously as servers and clients. A database 310 or databases, coupled to the server computer(s), stores much of the web pages and content exchanged between the user computers. The server computer(s), including the database(s), may employ security measures to inhibit malicious attacks on the system, and to preserve integrity of the messages and data stored therein (e.g., firewall systems, secure socket layers (SSL), password protection schemes, encryption, and the like).

The server computer 308 may include a server engine 312, a web page management component 314, a content management component 316 and a database management component 318. The server engine performs basic processing and operating system level tasks. The web page management component handles creation and display or routing of web pages. Users may access the server computer by means of a URL associated therewith. The content management component handles most of the functions in the embodiments described herein. The database management component includes storage and retrieval tasks with respect to the database, queries to the database, read and write functions to the database and storage of data such as video, graphics and audio signals.

Many of the functional units described herein have been labeled as modules, in order to more particularly emphasize their implementation independence. For example, modules may be implemented in software for execution by various types of processors, such as processor 201. An identified module of executable code may, for instance, comprise one or more physical or logical blocks of computer instructions which may, for instance, be organized as an object, procedure, or function. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

B. System Components

Figure 4:
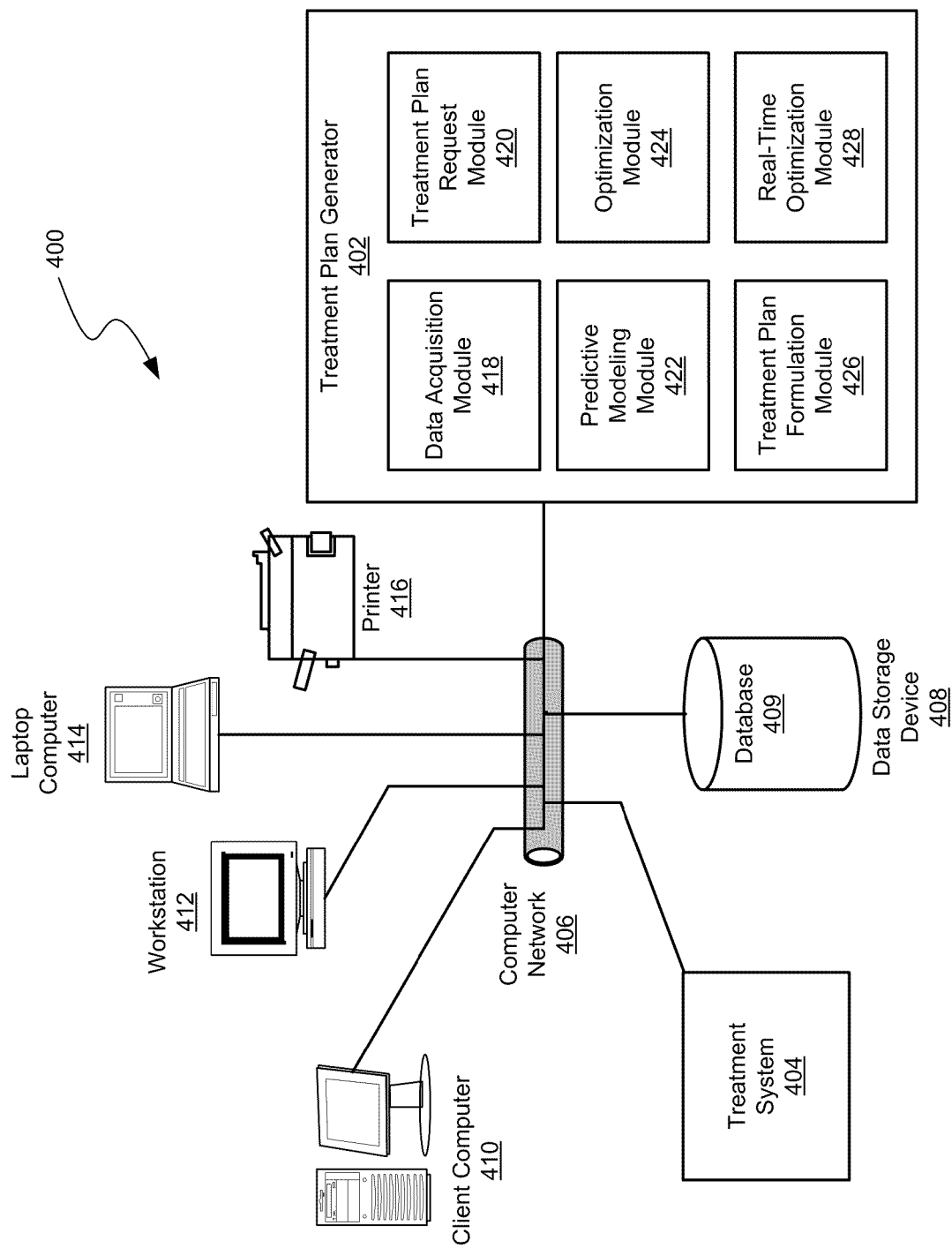
FIG. 4 is a schematic block diagram illustrating a treatment planning system for generating patient-specific treatment plans and anticipated treatment results in accordance with an embodiment of the disclosure.

FIG. 4 depicts a treatment planning system 400 for generating patient-specific treatment plans and anticipated treatment results in accordance with an embodiment of the disclosure. Use of the system 400 can provide medical practitioners with technical tools for capturing data related to a patient's pre-treated target region as well as desired post-treatment outcome, and analyzing the data sets relative to a priori (e.g., reasoned information, computer-simulated-derived, general information known in the art, etc.) and/or empirically-derived (e.g., clinical treatment of prior patients) information specific to the treatment type. The system 400 can further provide medical practitioners with tools for calculating best-fit treatment parameters for achieving as near as possible the desired post-treatment outcome, and communicating an anticipated post-treatment outcome to the patient. For example, in some embodiments, the medical practitioner can use the system 400 to generate visual images of a patient's pre-treated target region as well as generate simulated images depicting the anticipated post-treatment outcome. The simulated image can be generated from the a priori and/or empirically-derived information stored and accessed from database(s), or in another embodiment, the simulated image can be created by the system user (e.g., the medical practitioner, system technician, etc.) through graphic manipulation. The system 400 can generate one or more patient-specific treatment plans for achieving the desired and/or anticipated post-treatment outcome, and in some embodiments, direct treatment systems to implement the treatment plan.

The system 400 includes a treatment plan generator 402, which can reside on a server such as server 308, in communication with client computers, such as personal computer 410, workstation 412, laptop computer 414, etc. ("client computer"), through a computer network 406. The computer network 406 can be substantially similar in structure and function to computer network 306. The treatment plan generator 402 can be in communication with a data storage device 408 which can be a repository for one or more databases 409. The system 400 can also include a printer 416, and/or other devices in communication with the treatment plan generator 402 through the computer network 406.

The treatment plan generator 402 is capable of receiving patient-specific data and other information relating to treatment plan requests, comparing patient-specific data to the a priori and/or empirically-derived information stored and accessed from database(s) 409, calculating a best-fit combination of treatment parameters and formulating a treatment plan specific to a request. The requests and/or treatment plan(s) can be communicated through the computer network 406 to/from one or more requesting client computers. Medical practitioners conducting remote physical examinations in which a target region of a patient is manually examined by the practitioner, or a target region is imaged by one or more medical imaging devices, can enter, download, or otherwise input data into a client computer for transmitting the data to the treatment plan generator 402. Additionally, the treatment plan generator 402 and the network 406 can include other add-on systems (e.g., treatment system 404) arranged in other ways without departing from the spirit or scope of the present disclosure.

As described above, the treatment planning system 400 can include and/or be connected to a treatment system 404, such as the treatment system 100 described above and with reference to FIG. 1, via the network 406. In one embodiment, the treatment system 404 can include a treatment device for cooling subcutaneous lipid-rich cells, for example, to reduce adipose tissue thickness and/or change a body contour of a patient's target region. One of ordinary skill in the art will recognize additional embodiments in which a variety of treatment systems 404 suitable for use with treatment planning system 400 can be included. For example, the treatment system 404 can include any treatment device for applying positive heat transfer (i.e., increasing tissue temperature) or negative heat transfer (i.e., cooling/derceasing tissue temperature).

In some embodiments, the treatment planning system 400 can comprise, include and/or be connected with a treatment system 404 having one or more radio frequency electrode(s), having one or more ultrasound transducer(s) (e.g., for delivery of focused ultrasound (FU), high intensity focused ultrasound (HIFU) and/or low intensity ultrasound energy), one more laser(s), and/or other energy-emitting devices. For example, the treatment system 404 can be configured for delivery of HIFU energy, low frequency ultrasound energy, bipolar radio frequency energy, microwave energy, laser energy, infrared (IR) heat, etc. to a target region of a patient. In some embodiments, the treatment system 404 can cause subcutaneous lipid-rich cells to lyse or otherwise be selectively disrupted. In further embodiments, the treatment system 404 can cause denaturation of connective tissue, such as fibrous septae. In other embodiments, the treatment system 404 can include a device (e.g., vacuum, vibration applicator) or means for mechanical disruption of tissue. In other embodiments, the treatment planning system 400 can include a plurality of treatment systems 404 suitable for non-invasive and/or minimally invasive, alteration of a lipid-rich target region contour.

Examples of such devices and treatment systems are generally known in the art and described, e.g., in U.S. Patent and Patent Publication Nos. 6,071,239, 6,607,498, 7,258,674, 7,331,951, 7,347,855, 2005/0154314, 2005/0154431, 2005/0187495, 2006/0036300, 2006/0122509, 2007/0055156, 2007/0219540, 2007/0282318, 2008/0014627, 2008/0248554, 2008/0312651, 2009/0076488, 2009/0171253, and 2009/0221938. The disclosures of the above-referenced patents and patent publications are incorporated in their entirety herein by reference.

The treatment plan generator 402 can be associated directly with a provider of a priori and empirically-derived information relating to treatment plans. For example, the treatment plan generator 402 can be associated with a service provider or clinical database manager (e.g., hospital, privately or publicly held company, third party organization, etc.). In another embodiment, the treatment plan generator 402 can be associated directly with a provider and/or manufacturer of the treatment system 404. In some embodiments, the treatment plan generator 402 is in direct communication with the network 406, which can be operatively connected to medical institutions and/or medical service providers for providing efficient and efficacious treatment, and for providing a higher level of patient satisfaction during all stages (e.g., pre-treatment, treatment, and post-treatment phases) of elective and non-elective procedures. In a further embodiment not shown, the treatment plan generator 402 and data storage device 408 can be hosted directly on an individual client computer and be used to generate treatment plans in an on-site capacity. In this embodiment, the client computer and/or data storage device 408 may be connected to the network 406 for transmitting updated information (e.g., new treatment protocol information, data libraries, software updates, etc.) in real-time or in a periodic manner.

As illustrated in FIG. 4, the treatment plan generator 402 can include a data acquisition module 418, a treatment plan request module 420, a treatment modeling module 422, an optimization module 424 and a treatment plan formulation module 426. In other embodiments, the treatment plan generator 402 can also include one or more additional modules, such as a real-time optimization module 428, all of which will be described in detail below. In general, modules 418, 420, 422, 424, 426 and 428 comprise listings of executable instructions for implementing logical functions which can be embodied in any computer readable medium for use by or in connection with instruction execution system or device (e.g., computer-based system, processor-containing system, etc.).

The data acquisition module 418 can be included for receiving patient-specific pre-treatment data from the client computer (e.g., via operator input, file download, etc.), wherein the data relates to a specific patient. The data acquisition module 418 is further configured to create a patient-specific pre-treatment data set from the received pre-treatment data and, in one embodiment, deposit that data set into an existing pre-treatment data set library. The data acquisition module 418 can be configured to receive a plurality of data characterizing one or more target regions for medical treatment. In one example, a patient's target region characteristics and/or measurements are known and an operator can manually enter the data into a client computer and transmit the data to the treatment plan generator 402. In another example, the target region can be scanned or otherwise imaged using one or more medical imaging devices (e.g., ultrasound device, MRI, etc.), and the resulting image files, with embedded data, can be transmitted to the treatment plan generator 402. The data acquisition module 418 can receive and categorize the target region data, for example, by formatting the data and/or extracting the data from the one or more images. If additional data is required, the data acquisition module 418 can query the operator for the additional information during the data acquisition logic steps.

A pre-treatment data set can include general patient information such as gender, age, height, weight, etc. The pre-treatment data set can also include information characterizing the patient's target region, for example, the target area body position (e.g., abdominal, love handle, hip, buttocks, back, thigh, arms, knees, face, chin, etc.), the outer parameter of the effected region (e.g., shape, size, skin surface area, etc.), adipose tissue thickness, etc. In one embodiment, the data may indicate, or otherwise be assumed, that the adipose tissue at the target region has a uniform thickness. In another embodiment, the pre-treatment data set may provide more than one thickness measurements, wherein each measurement corresponds to one or more subset regions within the target region.

In some aspects of the disclosure, detailed information regarding positioning of target region (i.e., relative to one or more reference points) can be acquired using position sensing devices in communication with the client computer. For example, a treatment system applicator can include coupled position sensors. In an initial examination, a practitioner can place the applicator over the target region and place a single reference sensor at a position away from the target region. The client computer can receive position data indicating the exact position and orientation of the applicator relative to the reference sensor and transmit the position data to the treatment plan generator 402. In other embodiments, wands or other devices having position sensors or other infra-red and/or scanning capabilities can be used to extract position and orientation data of the target region.

In one embodiment, the pre-treatment data set may contain patient identification information, for example a patient's name or medical identification number for archiving and retrieval of the pre-treatment data set to/from the data storage device 408. In a further embodiment, the pre-treatment data set may include insurance billing and/or other billing information for automatic and efficient billing for treatment planning services rendered by the system 400. Although it has been described that general patient-specific information and data characterizing a patient's target region to be treated are included in the pre-treatment data set, it will be understood by those of ordinary skill in the art that general patient information can be created, maintained and/or updated in a separate patient-specific file associated with the system and/or database 409.

In yet another embodiment, the pre-treatment data set does not contain patient-specific identification information, such that patient identification information is not shared over the network 406 and/or cannot be determined by an operator accessing the treatment plan generator 402 or data storage device 408. In any of the above described embodiments, the data acquisition module 418 can assign the pre-treatment data set a unique patient identifier (e.g., unique identification number, etc.). For example, a unique identification number can be assigned on a priority basis and/or be generated in real-time by the data acquisition module 418. The unique identification number can encode information such as source (e.g., a medical provider office, a hospital, a specific client computer, etc.), date/time information, order of receipt, etc. Communication regarding the pre-treatment data set and/or other data sets and treatment plans associated with a particular patient can be communicated in a secure manner between the treatment plan generator 402 and a patient's provider using the unique identification number. Furthermore, security of medical data, such as the pre-treatment data set, can be ensured using encryption and decryption protocols known and appreciated by those of ordinary skill in the relevant art.

The data acquisition module 418 can also be configured to receive patient-specific objective post-treatment data from the client computer (e.g., via operator input, file download, etc.), wherein the objective post-treatment data relates to a desired post-treatment result. The data acquisition module 418 is further configured to create a patient-specific objective post-treatment data set (e.g., a desired and/or anticipated post-treatment data set). For example, the data acquisition module 418 can receive desired data elements relating to the expected or desired improvement to the pre-treatment status (e.g., adipose tissue reduction expressed in terms of percentage or millimeters, volume of adipose tissue removed, degree of change in body curvature and/or target area contour, etc.). The data acquisition module 418 can receive and categorize the objective post-treatment data, and in one embodiment, deposit the objective post-treatment data set into an existing objective post-treatment data library.

The treatment plan request module 420 can be provided to receive a treatment plan request from the client computer. In one embodiment, the request indicates a specific pre-treatment data set upon which to base the treatment plan. The treatment plan request module 420 is further configured to initiate a treatment plan generation session corresponding to the indicated pre-treatment data set. Following reception and categorization of patient-specific pre-treatment data by the data acquisition module 418, the treatment plan request module 420 can be invoked upon receiving a user request from a client computer to generate a treatment plan based upon at least one pre-treatment data set and, in some embodiments, at least one objective post-treatment data set. If a treatment plan is requested, the treatment plan request module 420 searches data storage device 408 to locate and retrieve 1) the patient-specific pre-treatment data set, and, if indicated, 2) the patient-specific objective post-treatment data set.

The treatment plan request module 420 can also retrieve a plurality of empirically derived and/or a priori data sets (the "model data sets") for comparison to the patient-specific data sets. The model data sets can include information such as the body position of the target region, the starting point data points (i.e., before actual and/or theoretical treatment), and the ending data points (i.e., actual and/or theoretical post-treatment results). The model data sets correspond to unique combinations of treatment parameters, wherein the treatment parameters were used (empirically) and/or modeled (a priori) to create the model data starting and ending data points.

The treatment plan request module 420 can invoke search and retrieve functions to collect the appropriate data sets from the appropriate databases 409. The predictive modeling module 422 can receive the accumulated set of search results from the invoked treatment plan request module 420 and rank the plurality of model data sets in accordance with a degree of affinity to the 1) pre-treatment data set, and, if included in the request, 2) objective post-treatment data set. Those of ordinary skill in the art will recognize that "ranking" means assigning an order of relative value to each model data set with respect to the other model data sets in the database 409.

For example, a relative ranking code may be assigned to each compared model data set with a predetermined range, such as 1-100. Alternatively, the compared model data sets may be ordered in accordance with their relative value; or, a combination of ordering and ranking codes may be utilized. In other various embodiments, compared model data sets may be dropped from the accumulated result set when the degree of affinity is below a pre-determined threshold value. The resulting collection, following the aforementioned ranking/pruning process, can be referred to as a sub-collection of model data sets from which data weighting, additional data entry and other optimization (via the optimization module 424) can reduce to a yet more refined sub-collection of model data sets.

In one embodiment, the predictive modeling module 422 can generate and transmit to the client computer a first graphical image representing the pre-treatment status of the patient's target region. For example, the predictive modeling module 422 can generate a graphical display of one or more of the highest ranked model data sets and/or a combination of model data sets to visually represent a best fit to the patient-specific pre-treatment data set. In another embodiment, the pre-treatment data set can be used to generate the first graphical image through computer-operated simulation programs and the like.

The predictive modeling module 422 can also be configured to generate and transmit to the client computer a second graphical image representing a desired post-treatment result/outcome. The second graphical image can be based on the first graphical image and the objective post-treatment data set. For example, the first graphical image can be a starting point from which to render the image by the desired specifications indicated in the objective post-treatment data set. In another embodiment, the second graphical image can be a graphical display of one or more of the highest ranked model data sets (e.g., from the highest ranked model data set, a composite of a plurality of highly ranked model sets, etc.), wherein the model data sets are ranked according to a level of affinity to the patient specific objective post-treatment data set. In some aspects of the disclosure, patient-specific objective post-treatment data may not be received. As such, the predictive modeling module 422 can be configured to generate a second graphical image representing a recommended post-treatment outcome.

In some embodiments, the first and second graphical images (i.e., "before" and "after" treatment images) can be displayed on a user interface screen display (described in more detail below) either simultaneously or sequentially such that the images can be used to assist communication to a system operator and/or patient. In other embodiments, the first and second graphical images can include representation of the pretreated target region and desired post-treatment result, respectively, in three-dimensions.

The optimization module 424 can be configured to receive additional data from the client computer and/or rewrite original or previous data received by the data acquisition module 418. In one embodiment, predictive modeling module 422 may require additional patient-specific pre-treatment data and/or objective post-treatment data to optimize the ranked order of the collection of model data sets from which a graphical display can be generated. As such, optimization module 424 can be invoked to query the client computer. In another embodiment, the optimization module 424 can receive instruction from a client computer (e.g., an optimization command) to alter output from the predictive modeling module 422. For example, graphical representation of pre-treatment status and/or post-treatment objective may not represent actual pre-treatment status and/or desired outcome. In this example, optimization module 424 can further query the user for additional information. The optimization module 424 transmits the updated patient-specific data to the predictive modeling module 422 for re-ranking the model data sets.

Upon realizing a final collection of model data sets (e.g., following optimization steps), the predictive modeling module 422 can, in one embodiment, generate one or more final graphical displays (e.g., modify the first and second graphical images, generate third and fourth graphical images, etc.) of one or more of the highest ranked model data sets and/or a combination of model data sets to visually represent the best fit to the patient-specific pre-treatment data set and post-treatment desires.

Also, upon realizing a final collection of model data sets, the treatment plan formulation module 426 can generate a patient-specific treatment plan to present to the user for implementation with the treatment system 404, such as treatment system 100 (FIG. 1). Treatment plan formulation module 426 can calculate the best-fit combination of treatment parameters from a plurality of possible treatment parameters (e.g., applicator size/shape and relative positioning on the target region, number of thermoelectric cooler (TEC) zones, number of ultrasound transducers, the type of ultrasound transducer, the arrangement and control setup of such transducers (e.g., use of one or more transducer matrices or arrays), number of radio frequency electrodes, the type of radio frequency electrodes, the arrangement of such electrodes, target temperature, duration of treatment, power, frequency, applicator movement velocity and pattern, and control parameters for features such as vibration, massage, vacuum, and other treatment modes) to generate the patient-specific treatment plan. In one embodiment, the treatment plan formulation module 426 calculates the best-fit combination of treatment parameters by determining the unique combination of treatment parameters corresponding to one or more model data sets having a highest affinity to the patient-specific data. The treatment plan formulation model 426 is also configured to output the patient-specific treatment plan to the client computer for treatment implementation.

For instance, in the case of HIFU therapy to selectively affect tissue such as subcutaneous adipose tissue, a number of parameters may be considered by treatment plan formulation module 426 in determining an optimal treatment plan. Such parameters include, by way of example only, and as described in, e.g., U.S. Pat. No. 7,258,674 and U.S. Patent Publication No. 2006/0122509: transducer movement (scanning or continuous modes vs. discrete or jumping modes) to affect continuous vs. discrete lesion fields, lesion pattern (e.g., linear, circumlinear, etc.), line of therapy spacing (e.g., between about 1 mm and about 10 mm), energy flux (e.g., between about 35 J/cm$^2$ and about 456 J/cm$^2$), frequency (e.g., between about 256 kHz and 6 MHz), power (e.g., between about 100 watts (acoustic) and about 378 watts (acoustic)), pulse repetition frequency (e.g., between about 1 kHz and about 10 kHz), burst length (e.g., between about 5 μsec and about 15 μsec), burst mode (continuous vs. pulsed), scan rate (e.g., between about 1 mm/sec and about 30 mm/sec), sweep velocity (e.g., between about 4 mm/sec and 25 mm/sec), focal depth for one or more transducers in an array (e.g., between about 0.10 cm and about 4.0 cm), on-off cycle time to promote cooling (e.g., between about 1 second and about 4 seconds), and so forth.

In the case of the use of microbubble solutions selectively to affect tissue such as subcutaneous adipose tissue as described in U.S. Patent Publication Nos. 2008/0014627 and 2008/0248554, other parameters may be considered by treatment plan formulation module 426 in determining an optimal treatment plan. Such parameters may include, by way of example only: microbubble type, state and composition (e.g., encapsulated vs. unencapsulated microbubbles, active or dissolved microbubbles, ambient air, oxygen, carbon dioxide, argon, hydrogen, perfluoropropane and mixtures thereof, etc.), liquid solution type and composition (aqueous, saline, degree of tonicity, buffering agents to control the pH of the liquid solution, surfactants, vasoconstrictors, anesthetics, etc.), liquid/microbubble ratio, microbubble size, degree of lysing capability, etc.), needle size and configuration, microbubble insertion rate and depth, type of ultrasound used to effect cavitation such as large duty pulsed signals, continuous wave signals (at frequencies, e.g., between about 500 kHz and 15 MHz), degree of energy focus (focused, unfocused, or defocused), mechanical index (e.g., between about 0.5 and about 1.9), transducer type and configuration, acoustic pressure (e.g., between about 100 kPa and 20 MPa), pulse repetition frequency (e.g., greater than 500 Hz), duration of insonation required to both distribute the microbubbles and to induce transient cavitation, and so forth.

In the case of the use of radio frequency heating selectively to affect tissue such as subcutaneous adipose tissue as described in, e.g., U.S. Patent Publication Nos. 2007/0282318, 2008/0312651, and 2009/0171253, other parameters may be considered by treatment plan formulation module 426 in determining an optimal treatment plan. Such parameters may include, by way of example only: radio frequency electrode geometric dimensions, type of coupling (e.g., capacitive or inductive), cooling modality (e.g., conduction, forced air, spray cooling, etc.), the use and rate of electrode movement during treatment, monopolar vs. bipolar configurations, frequency of the radio energy, electrode movement rate over the treatment area, cooling requirements, power level, treatment time, etc. Similarly, for the use of laser heating, other parameters such as power level, wavelength, dwell time, pulsed vs. continuous energy, type and degree of cooling used., etc. are examples of parameters that may be considered by treatment plan formulation module 426.

In the case of the use of minimally invasive techniques to cool or freeze adipose tissue described elsewhere herein by, e.g., one or more cryoprobes, other parameters may be considered by treatment plan formulation module 426 in determining an optimal treatment plan. Such parameters may include, by way of example only: cryogen gas temperature, type of cryogen, cryoprobe dimensions and configuration (e.g., length, diameter, tapered, cylindrical, etc.), the number of cryoprobes and, in the case of multiple cryoprobes, their configuration to effect a desired treatment (e.g., any number of two-dimensional or three-dimensional arrays, etc.), power level, depth of tissue insertion, orientation within the tissue, dwell time, and so forth.

Other techniques for effecting a desired treatment outcome may require other parameters; such parameters may be incorporated into the treatment plan formulation module 426 as desired.

The treatment plan formulation module 426 is configured to create a treatment plan that is comprehensive for achieving results. In one embodiment, treatment plan formulation module 426 utilizes additional a priori and empirically-derived information to account for natural diffusion rates of cold temperature through subcutaneous adipose tissue. For example, the present inventor recognized that cold temperatures diffuse to deeper levels as the thickness of the adipose tissue layer increases. In other embodiments, the treatment plan formulation module 426 utilizes a priori and empirically-derived information to account for applicator edge effects (i.e., temperature differences between the middle of the applicator plate and the edge of the applicator plate), and effects of more than one treatment sessions (e.g., adjacent target regions, overlapping target regions, etc.). In some embodiments, the treatment plan includes TEC zone specific parameters such that each zone is controlled independently of other zones.

In another embodiment, the system 400 facilitates periodic, ongoing evaluation of a patient's actual, monitored progress in response to the prescribed treatment. For example, a patient's response data can be collected and compared to the database 408 comprising empirically-derived data sets (e.g., clinical treatment of prior patients) and/or a priori data sets (e.g., reasoned information, computer-simulated-derived, general information known in the art, etc.) which are collectively referred to as the "model data sets". In one embodiment, one or more model data sets and associated treatment plans that rank with the highest affinity to the pre-treatment data set and desired post-treatment data set from the patient of interest are chosen from the database 408. The patient's progress at the particular point in time in the treatment course, e.g., pre-treatment, 1 month post-treatment, 6 months post-treatment, etc., can be compared relative to the efficiency and efficacy time line demonstrated by the one or more model data sets.

In the instances wherein the actual response matches the expected response, the information generated from the new patient can be added to the database 408. If the patient's treatment outcome differs from the anticipated post-treatment outcome, a root cause analysis can be performed to identify the source of the difference. For example, such an analysis could determine if the source of the difference is a result of patient-specific behavior (e.g., increased calorie consumption), medication-related effects, or patient-specific genetics or structural abnormalities not accounted for in the pre-treatment data set (e.g., greater than normal connective tissue in the target area, abnormal inflammatory response, etc.). Alternatively, the analysis could determine if the result difference was due to human error, such as measurement error or data entry error. In instances wherein the actual treatment result differs from the anticipated result, and wherein the root source analysis determined a verifiable cause for the difference that does not include human error, the information generated from the new patient can be added to the database 409. If the number of model data sets in the database 409 is n, then the information generated from the new patient can be added as the $n^{th}+1$ model data set. In some embodiments, such information may include additional data not routinely acquired during a pre-treatment examination. In these instances, the system's newly acquired data can be used for querying future operators for more information and/or for more refined predictive modeling using more or less model data sets for generating treatment plans for future patients.

In one embodiment, the actual results obtained from a first treatment session can be utilized in the predictive modeling and or optimization phases for generating future treatment plans for the same patient. In this embodiment, the treatment plan request module 420 can receive one or more unique identifier codes with the transmitted request. Presentation of the one or more unique identifiers can initiate a protocol run by the treatment plan request module 420 to retrieve the data sets corresponding to the one or more unique identifiers and preference (e.g., weight) these data sets with, or in another embodiment, over the model data sets when generating the predictive model (e.g., by the predictive modeling module 422) or when optimizing the treatment parameters (e.g., by the optimization module 424).

In some aspects of the present disclosure, the system provides for real-time optimization of the treatment plan. For example, once the treatment is in progress, the treatment system 404 provides the capability of real-time monitoring the actual patient response to the treatment. Real-time feedback data can be collected in the initial treatment stages and compared to the predicted modeling data generated and/or compiled by the predictive modeling module 422.

Accordingly, the treatment plan generator 402 can also include the real-time optimization module 428 configured to receive real-time feedback data during treatment administration from the client computer. When associated with the treatment system 100 (referred to in FIG. 1), the feedback data can include, e.g., heat flux measurements, such as detected by heat flux sensors in a treatment system applicator, and/or monitor power usage for drawing heat from a skin surface. The heat flux measurements can indicate the thickness of the subcutaneous adipose tissue, for example, by gauging the distance from the skin to underlying muscle. For example, the lower the temperature reading, the greater the thickness. In contrast, the thinner the subcutaneous adipose layer, the higher the initial temperature measurements (i.e., due to heat transfer from the underlying muscle tissue).

Heat flux measurements can indicate other changes or anomalies that can occur during treatment administration. For example, an increase in temperature detected by a heat flux sensor can indicate a freezing event at the skin or underlying tissue (e.g., dermal tissue). An increase in temperature as detected by the heat flux sensors can also indicate movement associated with the applicator, causing the applicator to contact a warmer area of the skin, for example. Methods and systems for collection of feedback data and monitoring of temperature measurements are described in commonly assigned U.S. patent application Ser. No. 12/196,246, entitled "MONITORING THE COOLING OF SUBCUTANEOUS LIPID-RICH CELLS, SUCH AS THE COOLING OF ADIPOSE TISSUE," filed on Aug. 21, 2008, which is incorporated herein in its entirety by reference.

In one embodiment, the heat flux measurements (e.g., feedback data) can be collected during initial stages of treatment at desired and/or pre-determined time intervals. For example, the feedback data can include heat flux measurements collected one time per minute for about the first 5 minutes to about 10 minutes of a treatment session.

In other embodiments, feedback data can include skin and/or other tissue and properties (such as, e.g., temperature, epidermal and dermal thickness, optical transmissivity, electrical conductivity/resistivity, thermal conductivity/resistivity, heat capacity, elasticity, tensile and shear strength, relative composition of various components such as lipids, water, collagen, etc.), data relating to the device used, such as, e.g., device position coordinates, device velocity measurements, pressure measurements, etc., as detected by, for example, temperature sensors, tracking sensors, accelerometers, and, e.g., hepatic sensors associated with the treatment system 404, and as generally described, e.g., in U.S. Patent and Publication Nos. 7,258,674, 7,347,855, 7,532,201, 2005/0154431, 2009/0024023, 2009/0076488, the disclosures of which are incorporated by reference herein in their entirety.

The real-time optimization module 428 can also be configured to compare the real-time feedback data to an anticipated feedback data. The anticipated feedback data can be based, for example, on the one or more model data sets having a highest affinity to the patient-specific data. In another embodiment, the predictive modeling module 422 can predict anticipated feedback data based on the pre-treatment data set, the best-fit combination of treatment parameters and/or additional empirically-derived and/or a priori information. The real-time optimization module 428 can also be configured to calculate a difference between the real-time feedback data and the anticipated feedback data. If the real-time feedback data is significantly different (i.e., difference is greater than a pre-determined threshold difference), the real-time optimization module 428 can modify the best-fit combination of treatment parameters to generate a modified treatment plan. The modified treatment plan can be transmitted from the real-time optimization module 428 to the client computer for changing treatment administration in real-time.

In some aspects of the disclosure, the patient-specific data received by the system 400 includes one or more objective post-treatment data elements and limited or no patient-specific pre-treatment data elements. In other aspects, the patient-specific data received by the system 400 includes estimated pre-treatment data elements. In these embodiments, the system can include a real-time optimization module 428 configured to receive real-time feedback data during treatment administration (e.g., preliminary and/or "explorative" treatment, etc.) from the client computer to determine actual target region pre-treatment data. The predictive modeling module 422 can be configured to receive and compare the actual target region pre-treatment data to the plurality of model sets, and to rank the plurality of model data sets in accordance with a degree of affinity to the actual target region pre-treatment data, and if provided, objective post-treatment data.

As described above, the treatment plan formulation module 426 can be configured to calculate the best-fit combination of treatment parameters to generate the patient-specific treatment plan. To calculate the best-fit combination of treatment parameters, the treatment plan formulation module 426 may determine the unique combination of treatment parameters corresponding to one or more model data sets having a highest affinity to the actual target region pre-treatment data and, if provided, objective post-treatment data. The real-time optimization module 428 can be configured to deliver the patient-specific treatment plan to the client computer in real-time. The treatment system 404 can be configured to receive the patient-specific treatment plan from the client computer in real-time and modify treatment parameters during treatment based on the treatment plan (e.g., in an automatic or semi-automatic manner).

In current practice, medical practitioners or clinicians rely heavily upon their own clinical experiences as well as trial and error methods for examining patients, designing a best-guess treatment protocol and formulating a treatment prescription for a particular patient. Typically, these conventional treatment protocols can be generic, such that multiple patients will be treated with the identical treatment protocol. The treatment can be executed using the prescribed treatment system; however, the generic and/or best-guess protocols and prescriptions can be subject to highly variable results and an unanticipated outcome in part because specific knowledge of the patient is not known when determining the treatment regimen.

In contrast, the systems and methods disclosed herein facilitate consistent and optimal results. Additionally, the system provides practitioners with communication and visual tools for rendering simulated images of anticipated results. These display tools allow a practitioner and/or a patient to visualize the anticipated results before engaging in the treatment course. Furthermore, upon visualizing the anticipated results, the practitioner and/or patient have opportunity to request changes and/or optimize the anticipated outcome based on additional subjective criteria and preferences. These requested changes can be incorporated into the final generated treatment plan.

In particular embodiments, the systems and methods for treatment planning provided herein can be applied to body contouring applications using the treatment system 100 described above with respect to FIG. 1, e.g., to remove excess subcutaneous adipose tissue by cooling (i.e., generating negative heat transfer). However, one of ordinary skill in the art will recognize that the treatment planning systems and methods as described herein may be applied to planning treatment protocols for a variety of medical applications. For example, the treatment planning system can be configured to incorporate other treatment systems for adipose tissue reduction, such as high intensity focused ultrasound (HIFU) radiation, radio frequency (RF) and/or light energy, minimally invasive applications for removing excess subcutaneous adipose tissue, etc. It is also anticipated that other medical procedures beyond those used for body contouring and adipose tissue reduction can employ the treatment planning systems and methods described herein. For example, physical therapy protocols and applications (e.g., for recovery following surgery) can be provided using the treatment planning systems and methods. In yet further embodiments, the treatment planning system can be configured to incorporate a plurality of treatment systems. In such embodiments, the treatment planning system can be used to assess a best-fit treatment plan by determining the most suitable regime among a host of regimes available.

C. Embodiments of User Systems and Interfaces

Figure 5:
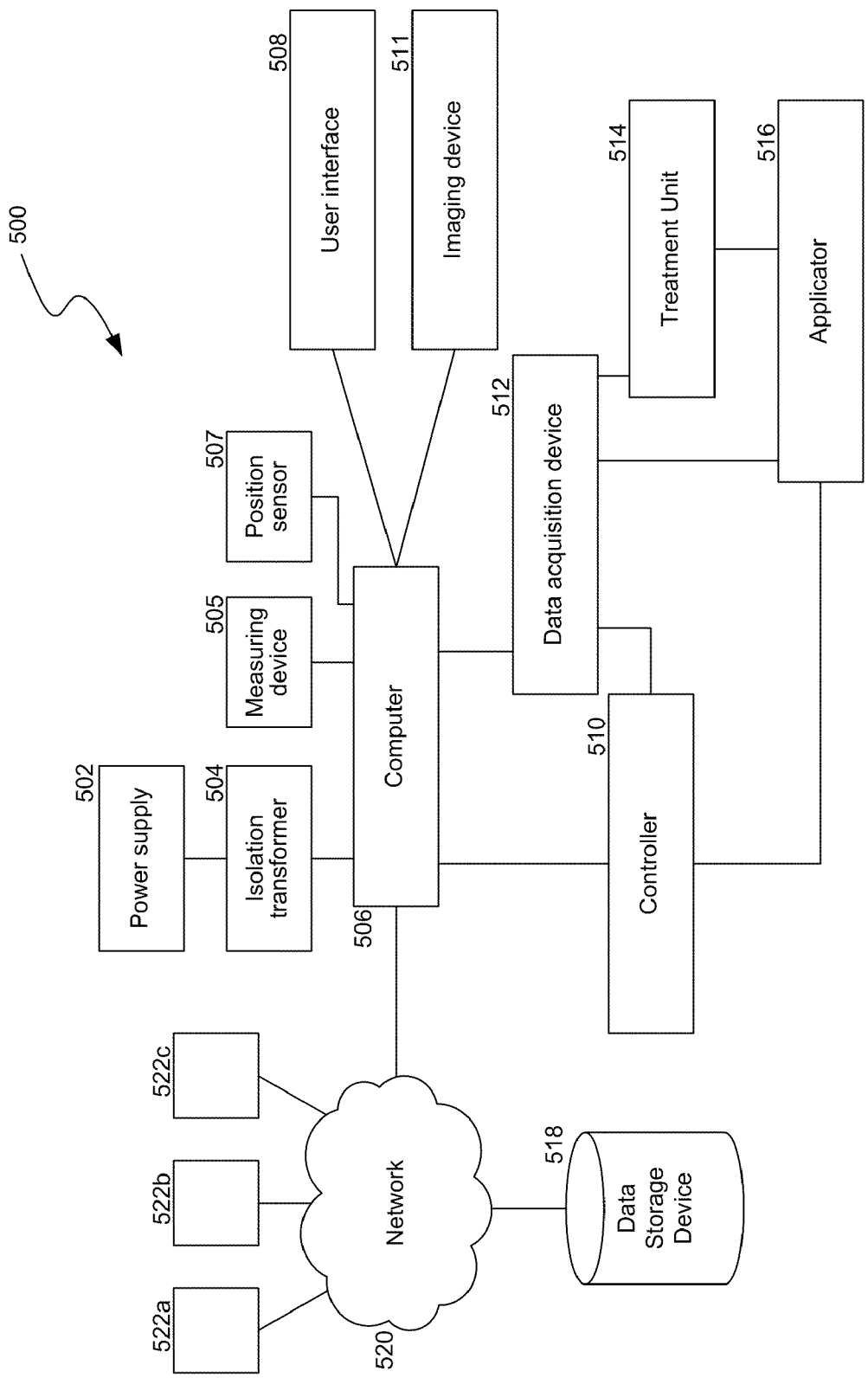
FIG. 5 is a schematic block diagram illustrating an environment in which the treatment planning system and treatment system may operate in accordance with an embodiment of the disclosure.

FIG. 5 is a schematic block diagram illustrating an environment in which the system may operate in some embodiments. The environment 500 includes a computing device 506 and a user interface 508. In the illustrated embodiment, the computing device 506 is integrated with a controller 510; however, in other embodiments, the computing device 506 can be a separate unit. For example, the computing device 506 can be any client computer described above with respect to FIG. 4. In another example, the computing device 506 can be a single board computer that is adapted for use within a housing of a treatment system controller 510. The environment 500 can also include a power supply 502 and, in medical treatment settings, an isolation transformer 504. The power supply 502 can be any ordinary type of power supply, such as alternating current or direct current. The isolation transformer 504 can be a medical grade transformer that isolates the patient from power fluctuations and problems, such as leakage current, voltage spikes or dips, and so forth.

The user interface 508 can include various input devices for collecting input from a user, such as an operator of the system, and can also include various output devices, such as for providing information to the operator, patient, and so forth. In some embodiments, the computing device 506 can be connected to the controller 510 to receive input from the controller and provide commands to the controller. Various components of the system may connect to other components via wired or wireless connections, such as Ethernet, serial (e.g., RS-232 or universal serial bus) connections, parallel connections, IEEE 802.11, IEEE 802.15, IEEE 802.16, "WiMAX," IEEE 1394, infrared, Bluetooth, and so forth.

The environment 500 can also include one or more imaging devices 511, such as medical imaging devices, connected to the computing device 506. For example, imaging devices can include a Magnetic Resonance Imaging (MRI) device, a Computed Tomography (CT) imaging device, an x-ray device, a camera, an ultrasound device, a surface profile scanning device, etc. In one embodiment, the computing device 506 can receive images and/or other related data generated from any one of devices 211.

In another embodiment, additional measuring devices 505 and/or position determination devices 507 can be connected to the computing device 506. Such devices may acquire data relating to the relative position of the target region to other anatomical or artificial reference points, target region surface area and shape, adipose tissue thickness, etc. In a specific example, the system can include a wand having a position sensor 507. The wand can relay information pertaining to relative position of the sensor with respect to a reference point or other fiduciary. Other measuring devices 505 may include calipers for pinching and measuring the thickness of subcutaneous adipose tissue, near-infrared interactance devices for transmitting infra-red light through the skin and detecting light reflection and adsorption by the underlying tissues, ultrasonic fat depth measuring devices, magnetic resonance imaging devices, etc. One of ordinary skill in the art will recognize other measuring devices and position determination devices for characterizing the subcutaneous adipose tissue of a patient's target region.

The computing device 506 can also connect to a data acquisition device 512. The data acquisition device 512 can acquire data from various components, such as the controller 510, a suitable treatment unit 514, an applicator 516, a patient protection device (not shown), and provide the retrieved data to other components, such as to the computing device 506. In various embodiments, the data acquisition device 512 can be incorporated into the controller 510 or applicator 516. As examples, the data acquisition device 512 can collect information such as how much power is being applied to treatment devices, the temperature at each treatment device, the temperature at the patient's skin, the status of the treatment unit, controller, or applicator, and so forth.

The computing device 506 may connect to network resources, such as other computers 522a-c and one or more data storage devices 518. As examples, the computing device 506 may connect to a server 522a to upload data logs, patient information, use information, and so forth. The computing device 506 may also connect to a server 522b to download updates to software, lists of applicators or patient protection devices that should be disabled, and so forth. The treatment plan generator 402 can reside on any one of servers 522a-c, and accordingly, treatment plan requests can be transmitted through network resource connections. The computing device 506 can also connect to the data storage device 518, such as the data storage device 408 containing a priori information and empirically derived information for generating treatment plans. As described above, the computing device 506 may connect to network resources via a network 520, such as the Internet or an intranet.

Figure 6:
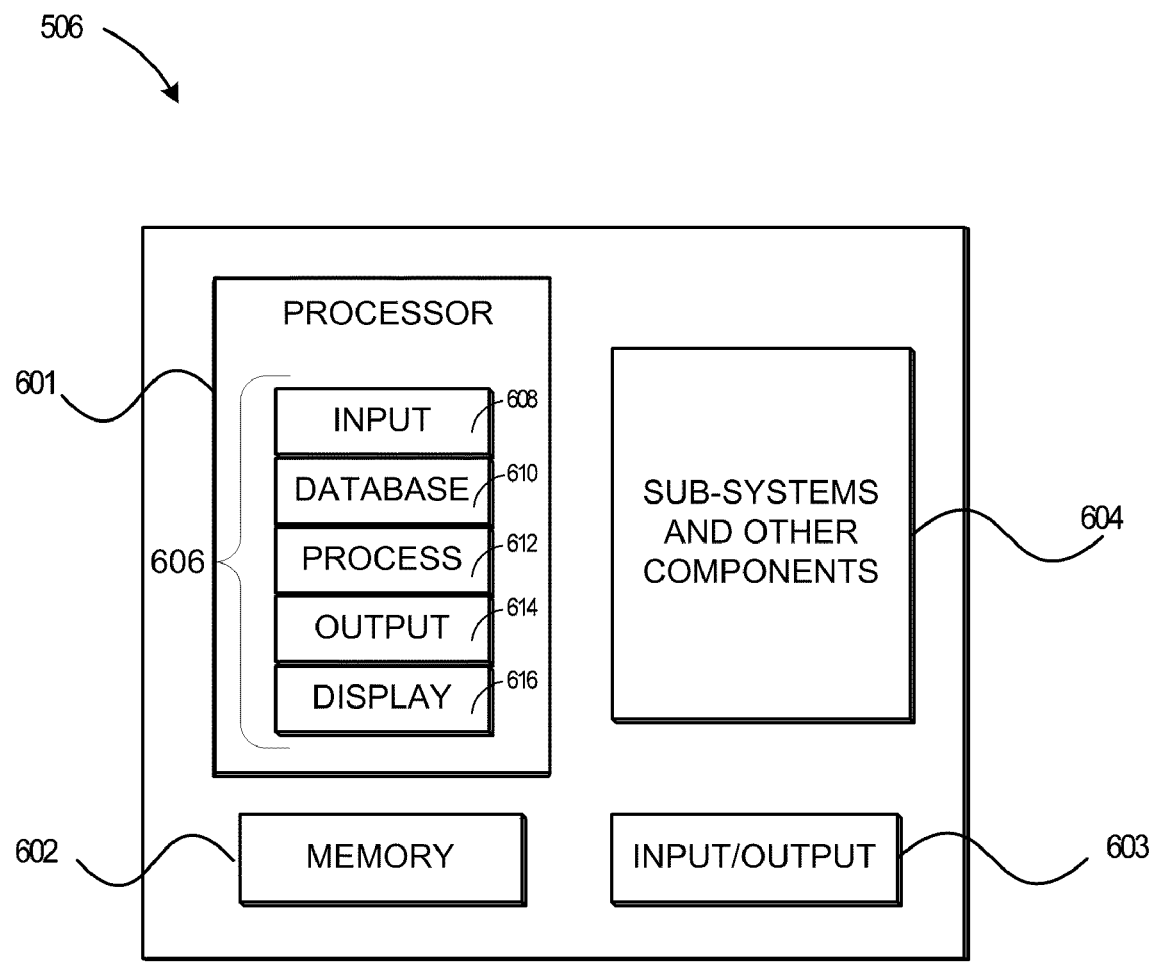
FIG. 6 is a schematic block diagram illustrating subcomponents of the computing device of FIG. 5 in accordance with an embodiment of the disclosure.

FIG. 6 is a schematic block diagram illustrating subcomponents of the computing device 506 of FIG. 5 in accordance with an embodiment of the disclosure. The computing device 506 can include a processor 601, a memory 602 (e.g., SRAM, DRAM, flash, or other memory devices), input/output devices 603, and/or subsystems and other components 604. The computing device 506 can perform any of a wide variety of computing processing, storage, sensing, imaging, and/or other functions. Components of the computing device may be housed in a single unit or distributed over multiple, interconnected units (e.g., though a communications network). The components of the computing device 506 can accordingly include local and/or remote memory storage devices and any of a wide variety of computer-readable media.

As illustrated in FIG. 6, the processor 601 can include a plurality of functional modules 606, such as software modules, for execution by the processor 601. The various implementations of source code (i.e., in a conventional programming language) can be stored on a computer-readable storage medium or can be embodied on a transmission medium in a carrier wave. The modules 606 of the processor can include an input module 608, a database module 610, a process module 612, an output module 614, and, optionally, a display module 616.

In operation, the input module 608 accepts an operator input via the one or more input devices described above with respect to FIGS. 2 and 5, and communicates the accepted information or selections to other components for further processing. The database module 610 organizes records, including patient records, pre-treatment data sets, generated treatment plans and operating records, post-treatment results, and other operator activities, and facilitates storing and retrieving of these records to and from a data storage device (e.g., internal memory 602, external database 518, etc.). Any type of database organization can be utilized, including a flat file system, hierarchical database, relational database, distributed database, etc.

In the example illustrated in FIG. 5, the process module 612 can generate control variables based on applicator sensor readings, treatment plan operational parameters, etc., and the output module 614 can communicate operator input to external computing devices and control variables to the controller 510. Referring to FIG. 6, the display module 616 can be configured to convert and transmit processing parameters, sensor readings, input data, treatment plan modeling and prescribed operational parameters through one or more connected display devices, such as a display screen, printer, speaker system, etc.

In various embodiments, the processor 601 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 602 can be standard memory, secure memory, or a combination of both memory types. By employing a secure processor and/or secure memory, the system can ensure that data and instructions are both highly secure and sensitive operations such as decryption are shielded from observation.

Referring to FIG. 5, the computing environment 500, and thereby the treatment planning system 400, can receive user input in a plurality of formats. In one embodiment, data is received from a user-operated computer interface 508 (i.e., "user interface"). In various embodiments, the user interface 508 is associated with the computing device 506 and can include various input and output devices, such as a keyboard, a mouse, buttons, knobs, styluses, trackballs, microphones, touch screens, liquid crystal displays, light emitting diode displays, lights, speakers, earphones, headsets, and the like. In other embodiments not shown, the user interface 508 can be directly associated with the controller 510 or the applicator 516.

FIGS. 7A-7D are views of a user interface 700 for interacting with the treatment plan generator 402 in accordance with an embodiment of the disclosure. It will be appreciated that the user interface, screen displays and information expressed via user interface described below in and depicted in FIGS. 7A-7D are exemplary only and are not intended to in any way limit the scope of the disclosure.

FIG. 7A is a view of a first display screen 702 of a user interface (UI) 700 for interacting with the treatment plan generator 402 (FIG. 4) in accordance with an embodiment of the disclosure. In one embodiment, the UI 700 is a graphical user interface (GUI) configured to allow a user to operate a software application, for example. The GUI can accept input via an integrated touch screen display and/or through devices such as a keyboard or mouse, and can provide graphical output on the computer display screen. In another embodiment, the UI 700 is a web-based user interface that can accept input and provide output by generating web pages. Input/output information is transmitted via the internet or other network and viewed by the user using a network browser or other interface, for example. In web-based applications, display pages can include known internet browser functions (e.g., address fields, back/forward buttons, refresh, other menu options, etc.) which operations are familiar to those of ordinary skill in the art and are not further explained.

A user of the treatment planning system 400 can engage the UI 700 to send and/or retrieve information regarding one or more patients during treatment planning sessions. As illustrated in FIGS. 7A-7D, the UI 700 includes one or more data entry display screens for initiating and completing a treatment planning session. Referring to FIG. 7A, the display screen 702 can include a plurality of data entry fields and/or drop down menus that are typically present with known browser technology as well as other windows based applications. As an example, display screen 702 can provide an entry area 704 for the user to enter non-topical data (e.g., practitioner identification data, patient identification data, etc.) to initiate a new treatment planning session, continue an existing treatment planning session, or to conduct follow-up on a treatment plan. For example, radial dial selectors 706 allow a user to select "new patient" or "existing patient." In one embodiment, an existing patient may include a patient that has had a previous treatment plan generated or partially generated. Once entry area 704 has been populated, the user can depress or "click" an ENTER button 708 to transmit the information.

FIG. 7B is a view of a second display screen 710 of the UI 700 responsive to user interaction with the first display screen 702 of FIG. 7A and in accordance with an embodiment of the disclosure. In the illustrated example, wherein the user selected "new patient", the display screen 710 includes an entry fields 712 for entering additional patient identification information (e.g., insurance plan information, medical identification number, etc.) and/or other non-topical data (e.g., age, gender, height, weight, prescription medication, medical conditions, skin type/color, etc.). The user can also indicate other attributes, such as the patient's pain sensitivity, total number of treatments desired, and so forth. Once entry fields 712 have been populated, the user can depress or "click" an ENTER button 714 to transmit the information.

FIG. 7C is a view of a third display screen 716 of the UI 700 responsive to user interaction with the second display screen 710 of FIG. 7B and in accordance with an embodiment of the disclosure. On the display screen 716, the UI 700 can display a unique identification code 718. For example, the treatment planning generator 402 (FIG. 4) may generate a patient-specific data file identifiable by the unique identification code 718 that optionally blinds the user to the patient's personally-identifiable information so that any privacy standards that the treatment situation may require may be met. A user can record the code 718 and/or use the code 718 for future retrieval or referral to the corresponding patient-specific data file. In the illustrated example, the display screen 716 can include target region data entry fields 720. For example, a user can select at field 722 a body region to be treated (e.g., love handle, abdomen, back, thigh, chin, buttocks, arms, face, knee, etc.). Data entry fields 720 can also include pre-treatment data entry fields 724, for entering data relating to target area surface area, adipose tissue thickness, etc. In some embodiments, a user may select if the tissue thickness is uniform or varied. If varied, a user may enter additional data relating to subsections of the target area. The display screen 716 may also include a file upload function 726 for retrieving and uploading pre-entered pre-treatment data and/or image files. Once entry fields 720 have been populated and/or files have been uploaded at 726, the user can depress or "click" an ENTER button 728 to transmit the information.

Following transmission of data entered at display screen 716, the treatment plan generator 402 may generate and transmit to UI 700 a pre-treatment graphical display or image (not shown) of the patient's target area. In one embodiment, the graphical display can be a three-dimensional rendering of the patient's target area. In some embodiments, the pre-treatment graphical display can be generated in part from extracted data from uploaded image files. In other embodiments, the pre-treatment graphical display can be generated from a combination of previously modeled images (from a database of modeled generic images and/or images associated with model data sets) and patient-specific pre-treatment data entered at display screens 710 and 716. In some embodiments, if the rendered graphical display does not accurately depict actual target area appearance, a user can enter additional data or revise data entry at display screen 716. The pre-treatment graphical display or image of the patient's target area may be complemented by data from one or more pre-treatment data entry fields 724 displayed as, e.g., alphanumeric characters, overlaid on the graphical display or image of the patient's target area corresponding to particular points or locations in the patient's target area. Such an overlay can be an efficient way to display large amounts of information in a manner that is readily discernable by the user. These data may alternatively or additionally be displayed on the display screen 716 of UI 700 in, e.g., tabular format, on different screens, etc. to provide maximum flexibility in the display of such information as desired by the user.

FIG. 7D is a view of a fourth display screen 730 of the UI 700 responsive to user interaction with the third display screen 716 of FIG. 7C and in accordance with an embodiment of the disclosure. In the illustrated example, the display screen 730 can include desired post-treatment outcome data entry fields 732, for entering parameters and/or data representative of a desired post-treatment outcome (e.g., percent adipose tissue thickness reduction, millimeter increments of adipose tissue reduction, +/− percent curvature change in contour profile, amount of volume reduction, etc.). Once entry fields 732 have been populated, the user can depress or "click" an ENTER button 734 to transmit the information.

Following transmission of data entered at display screen 730, the treatment plan generator 402 may generate and transmit to UI 700 a predicted post-treatment graphical display or image (not shown) of the patient's target area. In one embodiment, and as described above with respect to the pre-treatment graphical display, the predicted post-treatment graphical display can be a three-dimensional rendering of the patient's target area. In some embodiments, the predicted post-treatment graphical display can be generated in part from a simulation or manipulation of the pre-treatment graphical display. In other embodiments, the predicted post-treatment graphical display can be generated from a combination of previously modeled images (from a database of modeled generic images and/or images associated with model data sets), patient-specific pre-treatment data entered at display screens 710 and 716, and identified desired treatment results entered at display screen 730. In some embodiments, if the rendered graphical display does not accurately depict the desired post-treatment outcome, a user can enter additional data or revise data entry at display screens 716 and/or 730. In one embodiment, weighting criteria for data in the database (i.e., a priori information and/or empirically-derived data stored in data storage device 408; FIG. 4) can be altered, and these effects can be shown through graphical display. As described above with reference to the pre-treatment graphical display, the predicted post-treatment graphical display or image of the patient's target area may be complemented by predicted post-treatment data displayed as, e.g., alphanumeric characters, overlaid on the graphical display or image of the patient's target area corresponding to particular points or locations in the patient's target area. These data may alternatively or additionally be displayed on the display screen 730 of UI 700 in, e.g., tabular format, on different screens, etc. to provide maximum flexibility in the display of such information as desired by the user.

A user e.g., medical practitioner) may use the pre-treatment graphical display and the predicted post-treatment graphical display to present to the patient a visual representation of the anticipated treatment outcome. Graphical representation of "before" and "after" states can be an effective means for communicating the achievable results of treatment and eliminating certain aspects of patient as well as practitioner uncertainty. In one aspect, the patient can have peace-of-mind regarding treatment results prior to engaging in treatment. In another aspect, if the predicted post-treatment graphical display does not appeal or is otherwise unsatisfactory to the patient, a user can change desired outcome parameters to achieve a more desirable post-treatment result.

It is anticipated that during treatment plan generation, simulations may be run for one or more treatment plans. Accordingly, simulations can provide data and/or graphical display corresponding to the likely post-treatment outcome for multiple treatment plans in a manner specific for a particular patient (i.e., using patient-specific data). The effects of the respective treatments can be visually represented to the practitioner and/or patient via the UI 700 prior to treatment administration.

In some embodiments, the UI 700 can display a treatment plan upon final approval of the input data and/or graphical displays. For example, the treatment plan generator 402 may transmit the treatment plan for display in graphs, tables, etc. The treatment plan can contain all the directive instruction for implementing the prescribed treatment.

In the instance where a user selects "existing patient" on display screen 702, different first, second and third display screens may be presented in response to user interaction with previous display screens. For example, a user may be prompted to input a unique identification code (e.g., to accommodate privacy considerations), or alternatively, other identification information such as patient name, medical identification number, etc., for identifying the existing patient data and/or identifying a previous treatment planning session. In some instances, a user can input follow-up treatment data via the UI 700. For example, a patient can be evaluated at various time points post-treatment and measurement, imaging files, and/or other subjective or objective observation can be entered into the system via UI 700.

As described in more detail below, the databases associated with the system 400 can be updated with new data and adaptively incorporate the new data into evaluation and generation of future treatment plans for the same patient and/or different patients. As such, entry of actual post-treatment results can increase the volume and variation of empirically-derived data in the database (discussed in more detail below with respect to FIG. 8).

D. System Data Structures

In various embodiments, the system 400 can employ data structures that are stored in memory, such as in memory associated with secure processors ("secure processor memory") or in secure memory associated with client computers. The system 400 can also employ data structures stored in memory associated with the data storage device 408. The data structures enable the system 400 to generate and implement treatment plans, ensure system integrity, and protect patient privacy. The data structures also enable the system 400 to model the predicted post-treatment outcome, and display the predictive models with both visual representation and treatment parameter schemes. Some of the data structures disclosed herein can be indicated for read-only access, write-only access, or read/write access. The type of access can be enforced via a combination of hardware and/or software. As an example, when a field of the data structure is marked for read-only access, various algorithms associated with the system 400 may not attempt to write to the field. Moreover, the data storage device 408 or memory device 602 (referring to FIG. 6) storing the data structure may also prevent the field from being written to. When a field is marked for read-only access, the field may nevertheless be writable before it is deployed, such as by the manufacturer or distributor. As an example, a special encryption key or authentication key may be employed to write to read-only data structure fields.

Figure 8:
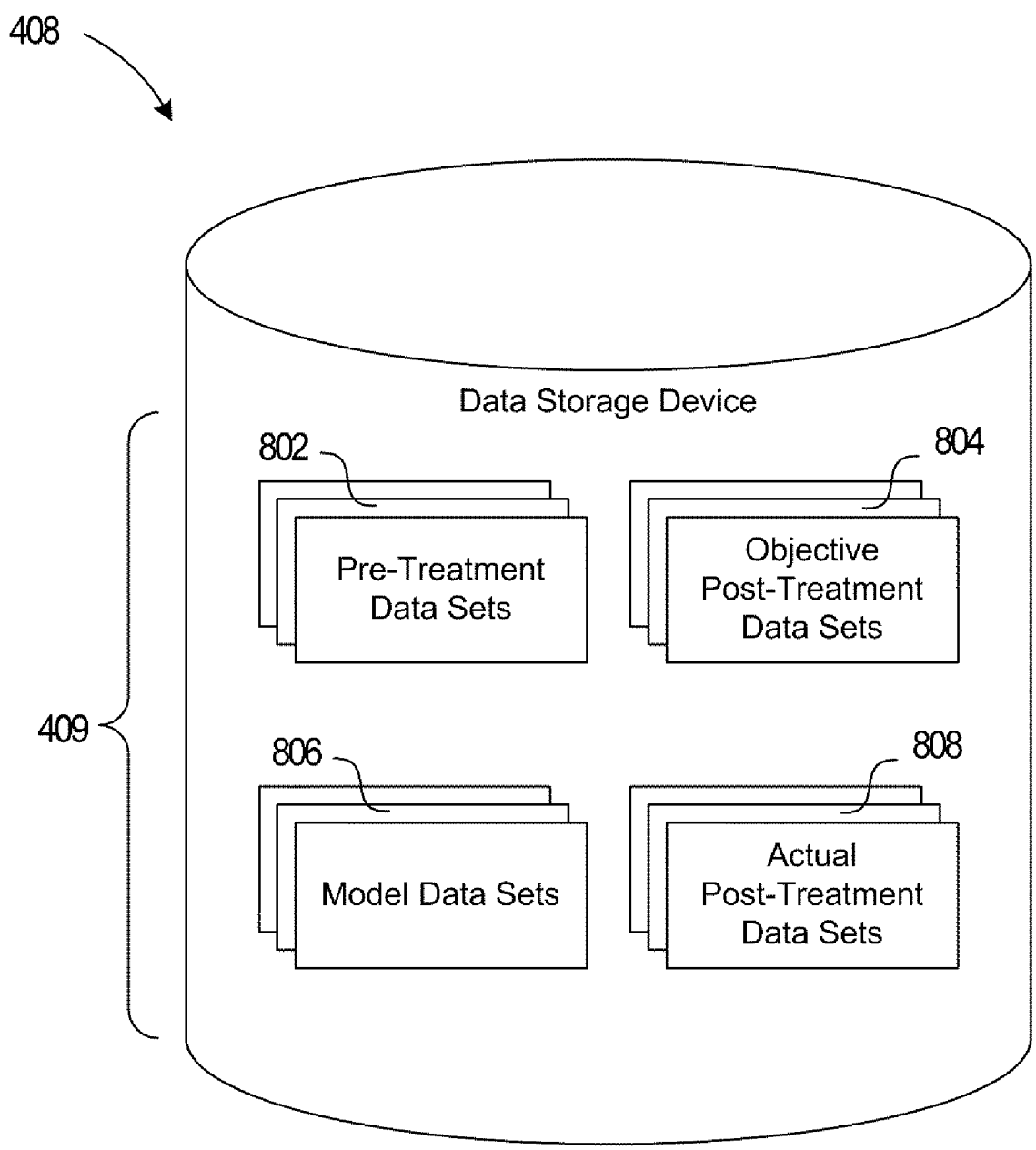
FIG. 8 is a schematic block diagram illustrating a data storage device employed by the treatment planning system of FIG. 4 in accordance with an embodiment of the disclosure.

FIG. 8 is a block diagram illustrating the data storage device 408 employed by the system 400 and FIG. 9 is a block diagram illustrating table data structures employed by the system 400 in accordance with various embodiments of the disclosure. While the data storage device 408 and the table data structures discussed below illustrate data structures with contents and organization that are designed to make them more comprehensible by a human reader, those skilled in the art will appreciate that actual data storage device 408 and data structures used by the system 400 to store information may take on other forms without departing from the scope or spirit of the present disclosure. For example, the data storage device 408 and/or illustrated data structures may be organized in a different manner, may contain more or less information than shown, may be compressed and/or encrypted; etc. Furthermore, the data stored in the data storage device 408 and/or data structures can be numerical, textual, graphical, etc. It is also anticipated that the one or more data sets and subsets can be organized, linked and retrieved in any manner suitable for the system 400.

Referring to FIG. 8, the data storage device 408 can include one or more databases 409, data libraries, and/or other empirically-derived and a priori information described herein. Database 409 and/or data libraries can include multiple data structures, each having one or more tables of accessible or archived information. In one embodiment, the database 409 can be a relational database and can include, multiple tables and/or data libraries pertaining to pre-treatment data sets 802, objective post-treatment data sets 804, predictive modeling data sets 806, actual post-treatment data sets 808, etc. It will be appreciated that any classification of data sets (e.g., pre-treatment, post-treatment, etc.) can be further broken down into subsets of data and the database 409 can include sub-tables within the primary table structure.

If a treatment plan is requested, treatment plan request module 420 searches data storage device 408 to locate and retrieve 1) pre-treatment data set, and 2) desired post-treatment data set, and predictive modeling module 422 compares the data sets to empirically derived and/or a priori data sets (the "model data sets"). As discussed above, treatment plan request module 420 can invoke search and retrieve functions to collect the appropriate data sets. As described above with respect to FIG. 4, the predictive modeling module 422 receives the accumulated set of search results from the invoked treatment plan request module 420 and ranks the model data sets in accordance with a degree of affinity to the 1) pre-treatment data set, and/or 2) desired post-treatment data set.

Referring to FIG. 9, relational database table 900 illustrates one embodiment of a treatment plan request data search for high affinity model data sets, wherein user input data captured by the UI 700 is retained. As an example, table 900 includes patient-specific pre-treatment data set information captured by the user interface (UI) 700 at display screen 710 (FIG. 7B), display screen 716 (FIG. 7C) and 730 (FIG. 7D). In various embodiments, the table 900 is identified by the unique identification code 718 assigned to a patient-specific data file. Data captured in the table 900 can be representative of data entered by the user during its creation or as later modified. Column 910 comprises the categories of information collected corresponding to entry fields 712 (FIG. 7B), entry fields 724 (FIG. 7C) and entry fields 732 (FIG. 7D).

Column 920 comprises various sub-categories for each primary category. For example, table 900, column 920 sub-categorizes PATIENT into GENDER and AGE. Column 930 refers to the information elements corresponding to the various categories and sub-categories of column 910 and 920. Referring to FIGS. 7B-7D, in conjunction with FIG. 9, it is apparent that the exemplary informational and/or data elements represented in the display screens 710, 716 and 730, such as Female, Male, Age groups (e.g., 20-39, 40-54, 55-70), Target Region (e.g., Love Handle, Abdomen, Back, Thigh), Thickness ranges (e.g., 4-20 mm, 20-40 mm, +40 mm), Percent Reduction ranges (e.g., 1-5%, 5-10%, 10-15%, 15-20%) are accommodated in column 930 of table 900.

Column 940 represents the specified data values for each of the information elements of column 930. For example, once again using FIGS. 7B-D, it can be seen that the selection of the radial button associated with Female at data field 712 is captured in table 900 by the specification of "YES" in the row "PATIENT—GENDER—FEMALE—YES". In the like manner, all of the selections made with the user interface 700 for display pages 710, 716 and 730 are represented in the exemplary relational table 900. Other information elements and data values associated with display pages 702, 710, 716 and 730 are not included in exemplary table 900 in the interest of simplicity. However, those of ordinary skill in the relevant art will appreciate that table 900 will expand as necessary to accommodate all categories, sub-categories, information elements and data values specified by the user during a treatment planning session.

In various embodiments, additional data structures can be added, such as to store calibration data, diagnostic data, test data, security data (e.g., to store security keys), executable code, and so forth.

E. System Routines

The system invokes a number of routines. While some of the routines are described herein, one skilled in the art is capable of identifying other routines the system could perform. Moreover, the routines described herein can be altered in various ways. As examples, the order of illustrated logic may be rearranged, substeps may be performed in parallel, illustrated logic may be omitted, other logic may be included, etc.

Figure 10:
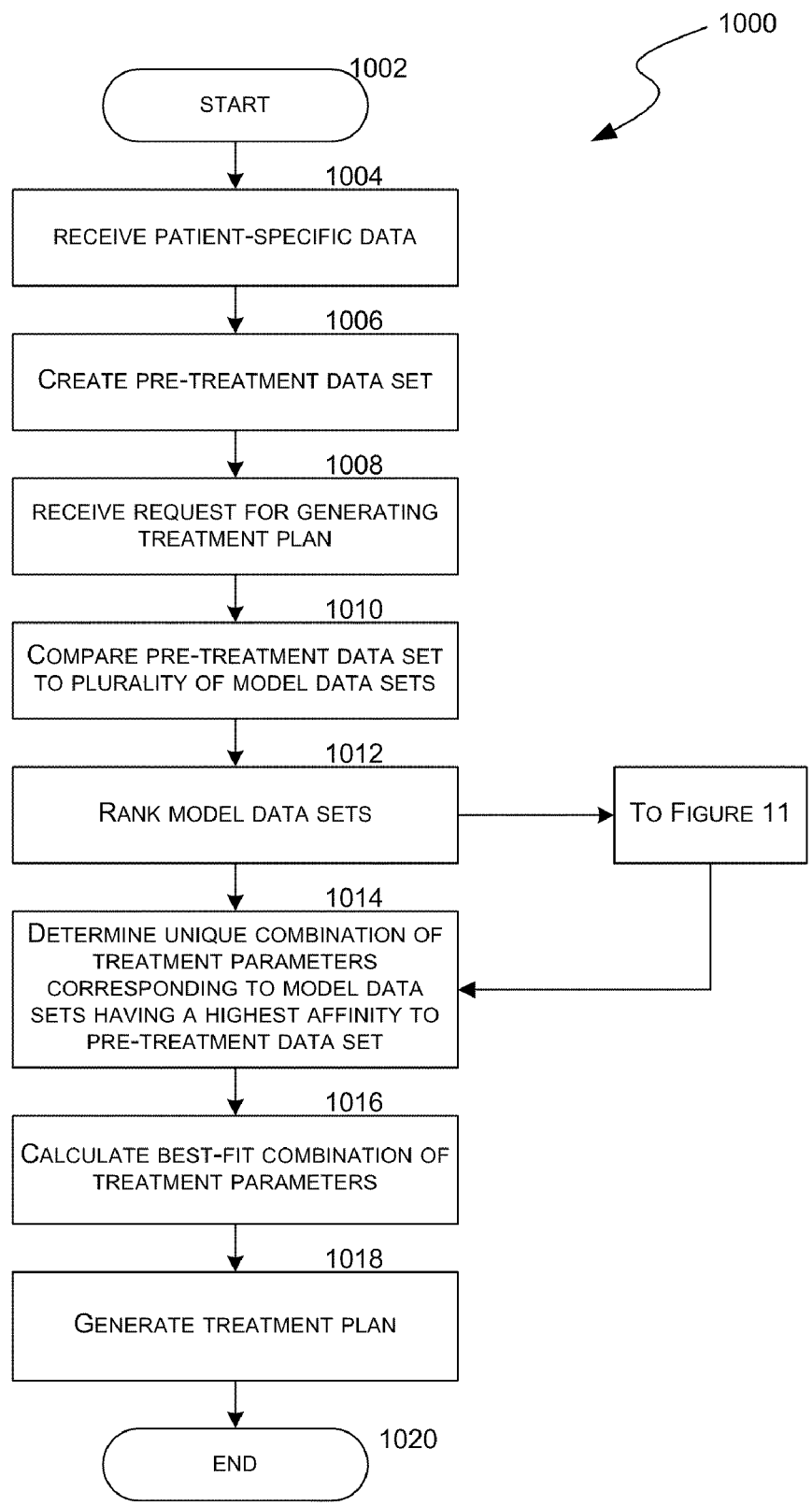
FIG. 10 is a flow diagram illustrating a routine for generating a patient-specific treatment plan invoked by the treatment planning system in accordance with an embodiment of the disclosure.

FIG. 10 is a flow diagram illustrating a routine 1000 for generating a patient-specific treatment plan invoked by the system in some embodiments. The routine 1000 can be invoked by a computing device, such as a client computer or a server computer coupled to a computer network. In one embodiment the computing device includes treatment plan generator. As an example, the computing device may invoke the routine 1000 after an operator engages a user interface in communication with the computing device.

The routine 1000 begins at block 1002 and the data acquisition module receives patient-specific data (e.g., general patient information, target region pre-treatment data, etc.) (block 1004) and creates a pre-treatment data set comprising target region data elements (block 1006). In some embodiments, the treatment plan includes a treatment plan for non-invasive, transdermal removal of heat from subcutaneous lipid-rich cells of a patient. In these embodiments, the patient-specific data can relate to target region body position (e.g., love handle, abdomen, thigh, buttocks, back, arms, face, chin, knees, etc.) and/or a subcutaneous adipose tissue thickness. In one embodiment, the thickness of the subcutaneous adipose tissue is estimated. In other embodiments, the thickness is measured with one of a plurality of measuring techniques (e.g., a pinch test, calipers, etc.). In still further embodiments, the thickness may be determined from one or more imaging techniques (e.g., ultrasound, MRI, CT, etc.). In some embodiments, the data acquisition module also receives patient-specific objective post-treatment data (e.g., desired post-treatment results, etc.) and creates an objective post-treatment data set (not shown).

The treatment plan request module receives a request for generating a patient-specific treatment plan (block 1008). The predictive modeling module compares the pre-treatment data set to a plurality of model data sets (block 1010). The model data sets can include at least one of empirically-derived data and a priori information. Additionally, the model data sets can correspond to unique combinations of possible treatment parameters. For example, possible treatment parameters for use with the treatment system 100 (with reference to FIG. 1) can include size, type and position of applicator, number of thermoelectric cooling zones, treatment time duration and target temperature for each respective zone, number of treatments, etc. When the treatment planning system includes other or additional treatment systems 404 (with reference to FIG. 4), such as those delivering laser, radio frequency (RF) and ultrasound energies, generating positive heat transfer, delivering injectable materials, etc., the model data sets can correspond to additional or alternate treatment parameters such as, for example, number of piezoelectric elements in an HIFU transducer, number of RF electrodes, transducer size, focus length, ultrasound energy frequency, pressure, power (e.g., Watts), pulse repetition frequency, velocity and pattern of transducer movement, wavelength of laser, and other parameters as discussed previously herein, etc.

Following the comparing step, the predictive modeling module ranks the plurality of model data sets in accordance with a degree of affinity to the pre-treatment data set (block 1012). Additionally, the treatment plan generation module determines the unique combination of treatment parameters corresponding to one or more model data sets having a highest affinity to the pre-treatment data set (block 1014). In one embodiment, the one or more model data sets having the highest affinity to the pre-treatment data set include model data sets having an affinity over a pre-established threshold affinity.

At block 1016, the treatment plan formulation module calculates a best-fit combination of treatment parameters from the unique combination of treatment parameters corresponding to the one or more model data sets having the highest affinity. In one embodiment, the best-fit combination can be a composite of treatment parameters corresponding to multiple model data sets. In another embodiment, the best-fit combination can include the unique combination of treatment parameters corresponding to a single model data set. The treatment plan formulation module also generates the patient-specific treatment plan for implementation by a treatment system. The treatment plan includes the best-fit combination of treatment parameters. In some embodiments, the computing device is in communication with the treatment system, and the treatment plan can be automatically implemented using the treatment system without requiring an operator to manually input the treatment parameters into a treatment system controller. The routine 1000 may then continue at block 1020, where it ends.

Figure 11:
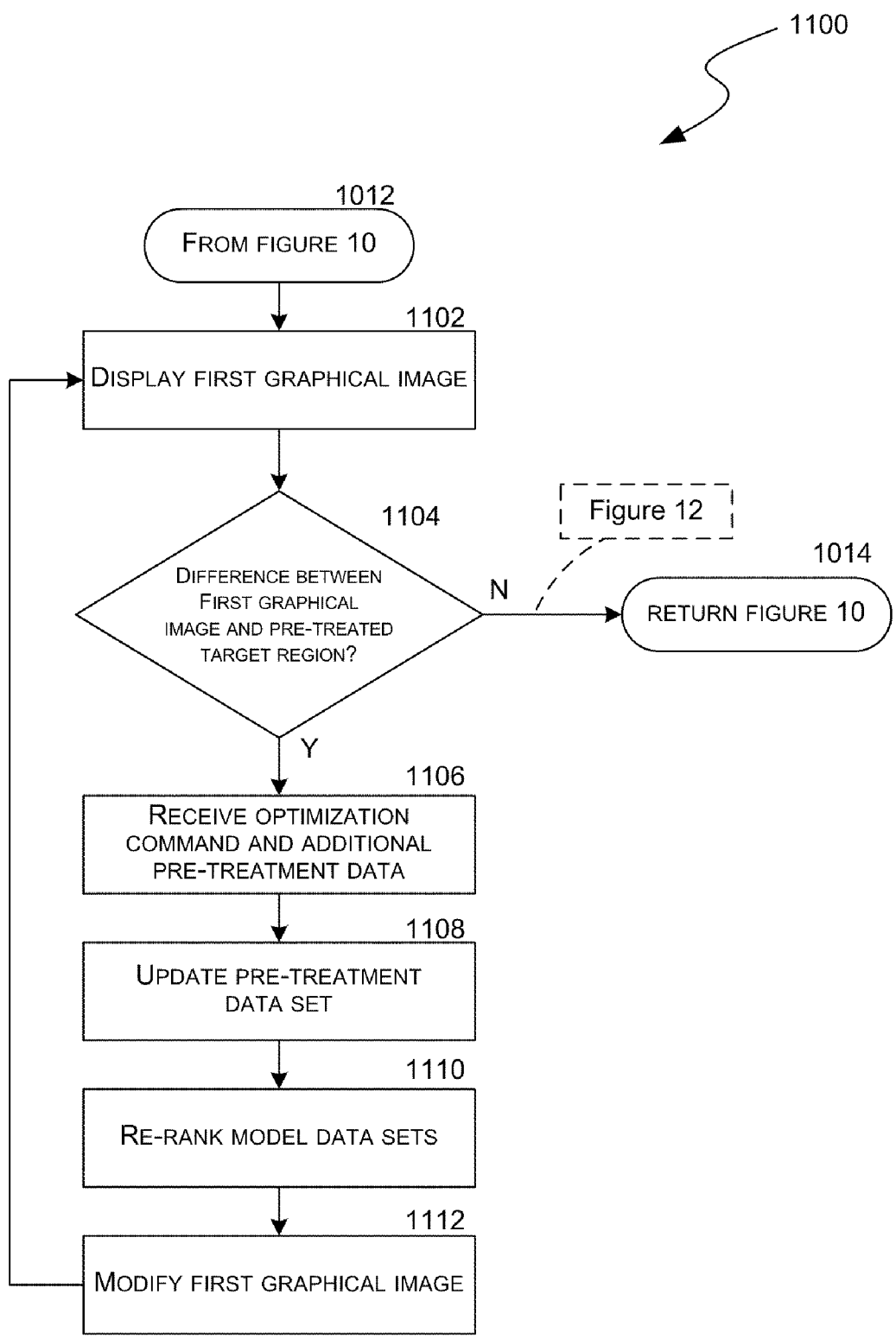
FIG. 11 is a flow diagram illustrating a routine for displaying graphical images invoked by the treatment planning system in accordance with an embodiment of the disclosure.

FIG. 11 is a flow diagram illustrating a routine 1100 for displaying graphical images invoked by the system in some embodiments. The routine 1100 can be invoked by the computing device of FIG. 10. The routine 1100 begins at block 1012 of FIG. 10 and the predictive modeling module displays a first graphical image, wherein the first graphical image represents the pre-treatment data set (block 1102). In one embodiment, the first graphical image is displayed on a user interface screen display visible to a system operator. In other embodiments, the first graphical image is printed, projected, emailed, etc., for visualization by a system operator.

At decision block 1104, the routine 1100 determines whether there is a significant difference between the first graphical image and the actual pre-treated target region of the patient. In various embodiments, the significance of the difference between the image of the pre-treated target region and the actual pre-treated target region can be specified by an operator, by additional patient-specific pre-treatment data, and so forth.

If there is a significant difference, the optimization module can receive an optimization command and/or additional pre-treatment data (block 1106). The optimization module also updates the pre-treatment data set (block 1108). In some embodiments, updating the pre-treatment data set includes addition of data to the data set. In other embodiments, updating the pre-treatment data set can include rewriting data in the pre-treatment data set to more accurately reflect the actual target region. Following update of the pre-treatment data set, the predictive modeling module re-ranks the model data sets (block 1110) and modifies the first graphical image (block 1112). If the first graphical image is modified in block 1112, the routine 1100 continues at block 1102 wherein the predictive modeling model displays the first graphical image. The routine 1100 may continue as before until no significant difference is detected between the first graphical image and the actual pre-treatment target region. The routine 1100 may then return to routine 1000 (FIG. 10) at block 1014.

Figure 12:
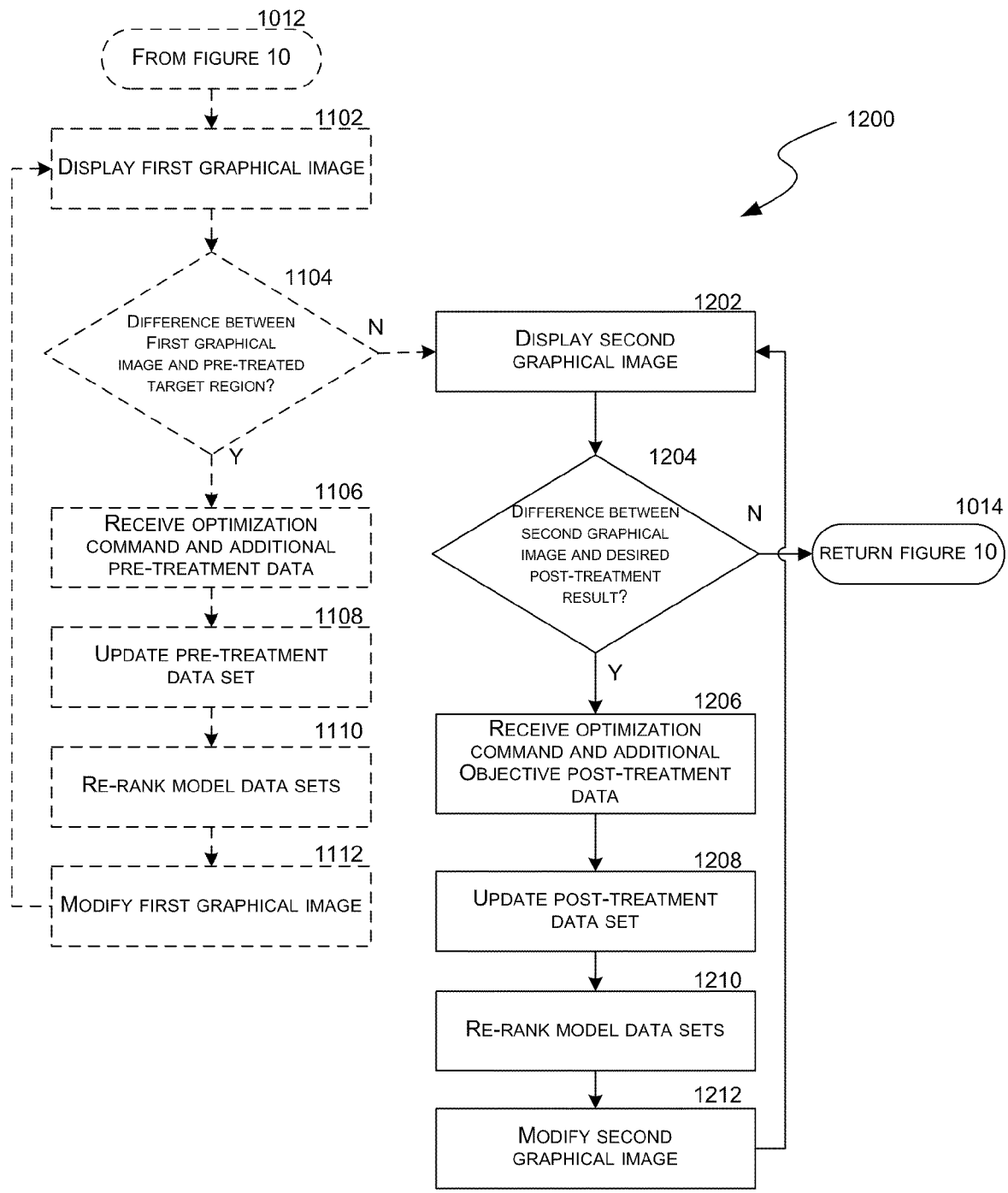
FIG. 12 is a flow diagram illustrating another routine for displaying graphical images invoked by the treatment planning system and in accordance with an embodiment of the disclosure.

As an alternative to returning to routine 1000 at block 1014, routine 1100 may continue with additional routine 1200. FIG. 12 is a flow diagram illustrating a routine 1200 for displaying graphical images invoked by the system in some embodiments. FIG. 11 logic steps have been illustrated in FIG. 12 in dotted lines. The routine 1200 can be invoked by the computing device of FIG. 10. The routine 1200 begins at decision block 1104 of FIG. 11. If the routine 1100 determines there is not a significant difference between the first graphical image and the actual pre-treated target region of the patient, the predictive modeling module displays a second graphical image, wherein the second graphical image represents a predicted post-treatment result (block 1202). In one embodiment, the second graphical image can be based on the first graphical image and other data such as objective post-treatment data. In other embodiments, the second graphical image can be generated by the predicative modeling module for representing a recommended and/or likely post-treatment outcome (e.g., based on a priori and/or empirically derived information). In one embodiment, the second graphical image is displayed on a user interface screen display visible to a system operator. In other embodiments, the second graphical image is printed, projected, emailed, etc., for visualization by a system operator.

At decision block 1204, the routine 1200 determines whether there is a significant difference between the second graphical image and a desired post-treatment result. In various embodiments, the significance of the difference between the image of the desired post-treatment result and the actual desired post-treatment result can be specified by an operator, by additional patient-specific objective post-treatment data and/or re-writing previously received objected post-treatment data, and so forth. In some embodiments, the operator may indicate that additional adipose tissue reduction is desired and/or different body curvature changes are desired.

As such, if there is a significant difference, the optimization module can receive an optimization command and/or additional objective post-treatment data (block 1206). The optimization module also updates the objective post-treatment data set (block 1208). In some embodiments, updating the objective post-treatment data set includes addition of data to the data set. In other embodiments, updating the objective post-treatment data set can include rewriting data in the objective post-treatment data set to more accurately reflect the desired post-treatment result. Following update of the objective post-treatment data set, the predictive modeling module re-ranks the model data sets (block 1210) and modifies the second graphical image (block 1212). If the second graphical image is modified in block 1212, the routine 1200 continues at block 1202 wherein the predictive modeling model displays the second graphical image. The routine 1200 may continue as before until no significant difference is detected between the second graphical image and the desired post-treatment result. The routine 1200 may then return to routine 1000 (FIG. 10) at block 1014.

In some embodiments, the first graphical image and the second graphical image can be displayed simultaneously, or in another embodiment, sequentially. As such, an operator may visualize and/or communicate to the patient the likely effect of treatment. For example, the first graphical image can represent a "before" image, and the second graphical image can represent an "after" image.

Figure 13:
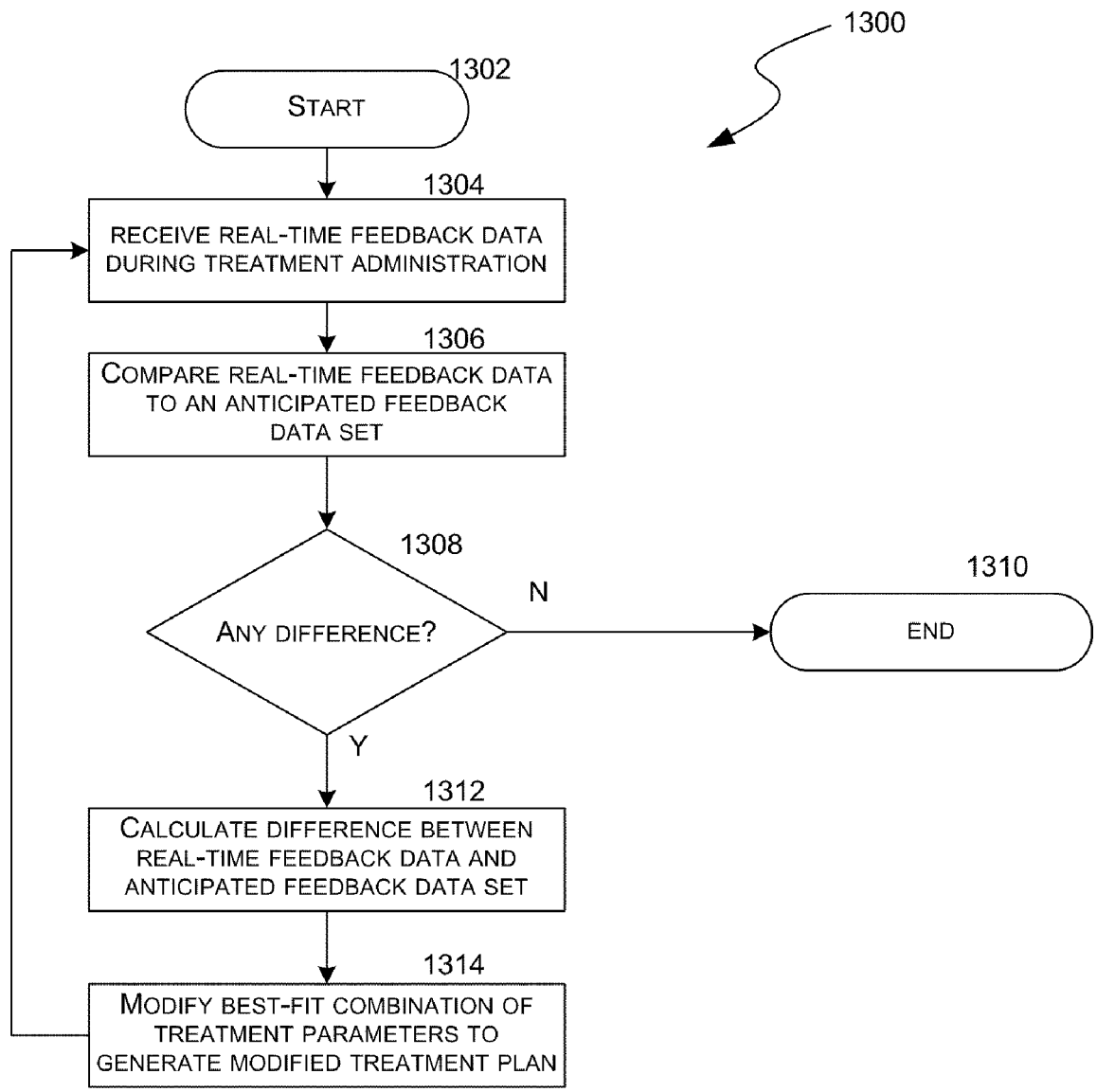
FIG. 13 is a flow diagram illustrating a routine for modifying a treatment plan in real-time invoked by the treatment planning system and in accordance with an embodiment of the disclosure.

FIG. 13 is a flow diagram illustrating a routine 1300 for modifying a treatment plan in real-time invoked by the system in some embodiments. The routine 1300 can be invoked by the computing device of FIG. 10. In one embodiment, the routine 1300 is invoked by a computing device in communication with a treatment system, such as the treatment system 100. Additionally, the routine 1300 can be invoked by the computing device for ensuring that treatment administration will achieve the desired post-treatment outcome as predicted by routines 1000 and 1200, for example.

The routine 1300 begins at block 1302 and the real-time optimization module receives real-time feedback data during treatment administration (block 1304). In one embodiment, the treatment system can be administering treatment according to a previously generated patient-specific treatment plan. In another embodiment, the treatment system can be administering treatment without a patient-specific treatment plan. In such an embodiment, the treatment system can administer a preliminary and/or generic treatment plan and the real-time optimization module can receive real-time feedback data to determine actual target region pre-treatment data. In one embodiment, the treatment system is configured to non-invasively and transdermally remove heat from subcutaneous lipid-rich cells of a patient. Feedback data can include heat flux measurements, for example, as detected by heat flux sensors in an applicator associated with the treatment system.

In other embodiments, the treatment system is configured to deliver positive heat transfer to subcutaneous lipid rich target regions of a patient. Such treatment systems may provide feedback data such as skin and/or other tissue and properties (such as, e.g., temperature, epidermal and dermal thickness, optical transmissivity, electrical conductivity/resistivity, thermal conductivity/resistivity, heat capacity, elasticity, tensile and shear strength, relative composition of various components such as lipids, water, collagen, etc.), data relating to the device used, such as, e.g., device position coordinates, device velocity measurements, pressure measurements, etc., as detected by, for example, temperature sensors, tracking sensors, accelerometers, and, e.g., hepatic sensors associated with the treatment system, and as generally described, e.g., in U.S. Patent and Publication Nos. 7,258,674, 7,347,855, 7,532,201, 2005/0154431, 2009/0024023, 2009/0076488, the disclosures of which are incorporated by reference herein in their entirety.

Following block 1304, the real-time optimization module compares the real-time feedback data to an anticipated feedback data set. In one embodiment, the anticipated feedback data set is based on the one or more model data sets having a highest affinity to the patient-specific pre-treatment and/or objective post-treatment data sets, as well as the best-fit combination of treatment parameters. At decision block 1306, the routine 1300 determines if there is a difference between the real-time feedback data and the anticipated feedback data set. If no significant difference is detected, the routine 1300 can end at block 1310. In this embodiment, treatment administration can continue without altering treatment parameters and/or treatment routines invoked by the treatment system. In some embodiments, the difference between the real-time feedback data and the anticipated feedback data set must exceed a pre-determined threshold difference for the routine 1300 to modify a treatment plan.

If the difference is significant (e.g., exceeds a pre-determined threshold level), the real-time optimization module calculates the difference between the real-time feedback data and anticipated feedback data to identify treatment parameters that can be modified (block 1312). At block 1314, the real-time optimization module modifies the best-fit combination of treatment parameters to generate a modified treatment plan. In some embodiments, the modified treatment plan can be administered in real-time. The routine 1300 may continue as before at block 1304 until no significant difference is detected between the real-time feedback data and the anticipated feedback data. The routine 1300 may then end at block 1310.

Figure 14:
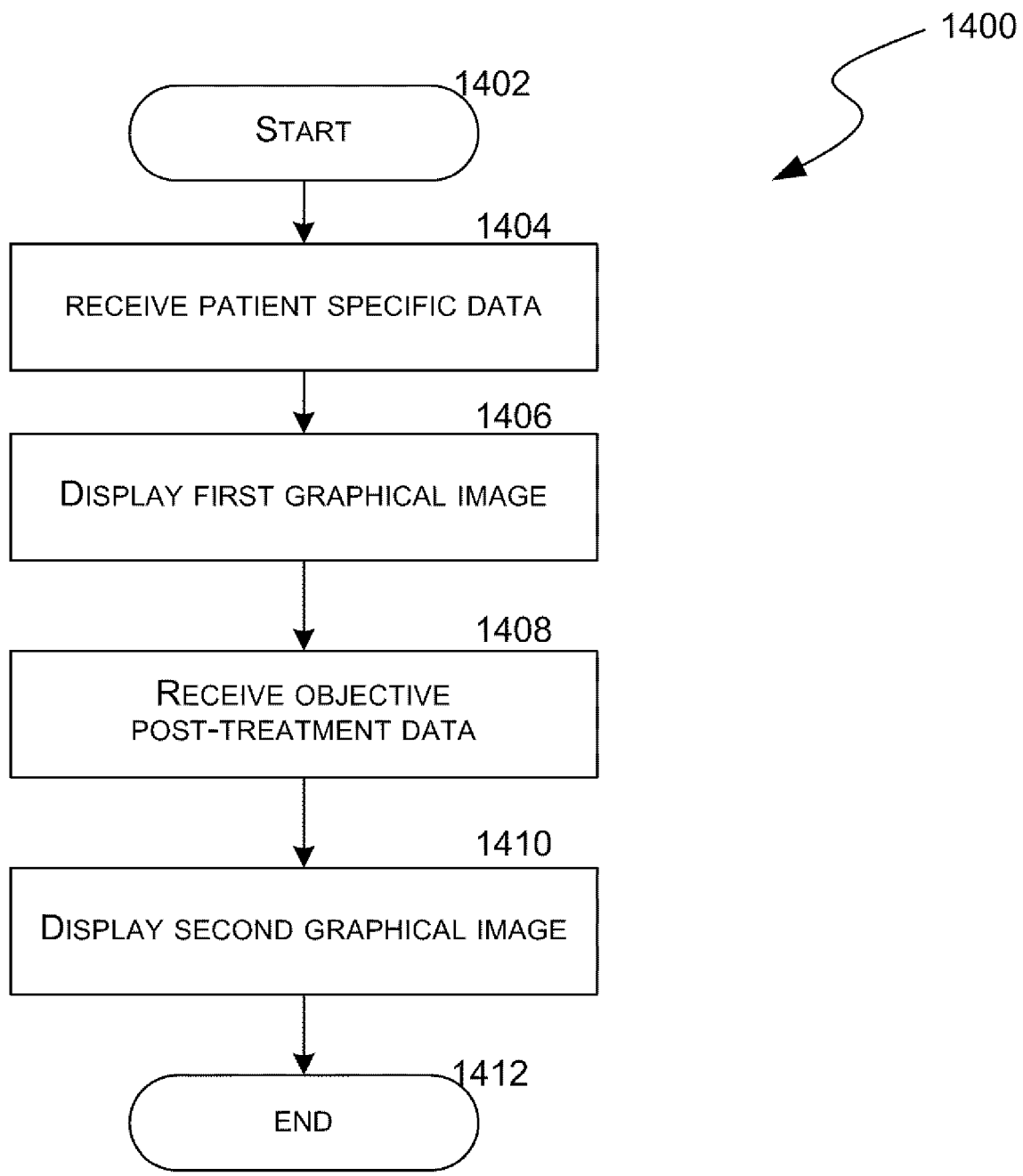
FIG. 14 is a flow diagram illustrating a routine for providing a user interface relating to generating a treatment plan invoked by treatment planning system and in accordance with an embodiment of the disclosure.

FIG. 14 is a flow diagram illustrating a routine 1400 for providing a user interface relating to generating a treatment plan invoked by the system in some embodiments. In some embodiments, the treatment plan can be for cooling a subcutaneous lipid-rich target region of a patient. The routine 1400 can be invoked by the computing device of FIG. 10. The routine 1400 begins at block 1402 and the system can receive patient-specific data (block 1404). At block 1406, the system can display a first graphical image. In one embodiment, the first graphical display represents the patient-specific data (e.g., pre-treatment target region data). Displaying the first graphical image can include displaying the image on a user interface display screen, for example. In one embodiment, the first graphical image includes visual representation of the patient-specific data in three-dimensions. The system can receive objective post-treatment data (block 1408). The objective post-treatment data can include data relating to a desired treatment result (e.g., percent reduction in subcutaneous adipose tissue layer, degree of change in target region contours, etc.).

At block 1410, the system displays a second graphical image representing the desired post-treatment result. The second graphical image can be based upon the patient-specific data and the objective post-treatment data. In one embodiment, displaying the second graphical image can include displaying the image on a user interface display screen. In some embodiments, the second graphical image includes visual representation of the desired post-treatment outcome in three-dimensions. The routine 1400 may then continue at block 1412, where it ends.

In one embodiment, the first graphical image and the second graphical image can represent "before" and "after" images enabling the system to communicate with the operator and/or patient anticipated post-treatment results. In some embodiment, the system can receive additional patient-specific data for modifying the first graphical image and/or the second graphical image.

The computing device can receive the information collected at the user interface, information that the data acquisition device component collects, images collected by medical imaging devices, and information transmitted via the computer network (e.g., from servers, treatment planning generator, database(s), etc.), and take various actions, such as by querying a user interface to request user input, commanding the controller, transmitting data to networked servers and/or database(s).

F. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

I claim:

1. A system for generating a patient-specific treatment plan for non-invasive fat removal from a patient comprising:
   a computer network for transmitting information relating to a patient's target region, the target region comprising subcutaneous fat, wherein the information includes one or more of the treatment plan requests, data, images, and treatment plans;
   a client computer associated with a treatment provider and in communication with the computer network;
   a database connected to the computer network for storing a plurality of model data sets and a plurality of treatment parameters, wherein the plurality of model data sets include at least one of empirically-derived data and a priori information, and wherein the model data sets correspond to unique combinations of the treatment parameters; and
   a treatment plan generator in communication with the computer network and configured to receive patient-specific data and treatment plan requests from the client computer, compare patient-specific data to the plurality of model data sets in the database, and automatically calculate a best-fit combination of treatment parameters from the plurality of treatment parameters to generate the patient-specific treatment plan for non-invasively transdermally removing heat from the subcutaneous fat of the target region.

2. The system of claim 1 wherein patient-specific data includes pre-treatment data derived from a patient's target region and objective post-treatment data relating to one or more desired treatment results.

3. The system of claim 2 wherein the treatment plan generator comprises:
   a data acquisition module configured to—
      receive patient-specific pre-treatment data from the client computer to create a patient-specific pre-treatment data set, the pre-treatment data relating to at least the patient's subcutaneous fat at the target region;
      receive patient-specific objective post-treatment data from the client computer to create a patient-specific objective post-treatment data set, the patient-specific objective post-treatment data relating to a desired change in the patient's subcutaneous fat at the target region; and
      deposit the patient-specific pre-treatment and objective post-treatment data sets into one or more data set libraries stored in the database;
   a treatment plan request module configured to—
      receive a treatment plan request from the client computer, wherein the request indicates the patient-specific pre-treatment data set;
      retrieve the patient-specific pre-treatment data set, patient-specific objective post-treatment data set and the plurality of model data sets from the database; and
      initiate a treatment plan generation session, wherein the session corresponds to the indicated patient-specific pre-treatment and objective post-treatment data sets;
   a predictive modeling module configured to rank the plurality of model data sets in accordance with a degree of affinity to the patient-specific pre-treatment data set and the patient-specific objective post-treatment data set; and
   a treatment plan formulation module configured to calculate the best-fit combination of treatment parameters from the plurality of treatment parameters by determining the unique combination of treatment parameters corresponding to one or more model data sets having a highest affinity to the patient-specific data.

4. The system of claim 3 wherein the one or more model data sets having a highest affinity to the patient-specific data includes the model data sets having an affinity over a predetermined threshold affinity.

5. The system of claim 3 wherein the treatment plan generator further comprises an optimization module configured to:
   query the client computer to request additional patient-specific data;
   receive additional patient-specific data from the client computer and update at least one of patient-specific pre-treatment data set and patient-specific objective post-treatment data set; and
   transmit updated patient-specific data to the predictive modeling module for ranking model data sets.

6. The system of claim 3 wherein the treatment plan generator further comprises a real-time optimization module configured to:
   receive real-time feedback data during treatment administration from the client computer;
   compare the real-time feedback data to an anticipated feedback data based on the one or more model data sets having a highest affinity to the patient-specific data;
   calculate a difference between the real-time feedback data and the anticipated feedback data to create a patient-specific actual data set;
   modify the best-fit combination of treatment parameters to generate a modified treatment plan based on at least the patient-specific actual data set; and
   transmit the modified treatment plan to the client computer for changing treatment administration in real-time.

7. The system of claim 2 wherein the treatment plan generator is further configured to:
   generate a first graphical image representing the pre-treatment data; and
   generate a second graphical image representing a desired post-treatment outcome, wherein the second graphical image is based on the pre-treatment data and the objective post-treatment data.

8. The system of claim 2, further comprising a predictive modeling module configured to:
rank the plurality of model data sets in accordance with a degree of affinity to the patient-specific pre-treatment data set and the patient-specific objective post-treatment data set
transmit to the client computer a first graphical image representing the model data set having a highest degree of affinity to the patient-specific pre-treatment data set; and
generate and transmit to the client computer a second graphical image representing a desired post-treatment outcome, wherein the second graphical image is based on the first graphical image and the objective post-treatment data set.

9. The system of claim 8 wherein:
the treatment plan generator further comprises an optimization module configured to—
receive an optimization command from the client computer following transmission of the first graphical image or the second graphical image;
receive additional patient-specific data from client computer and update at least one of patient-specific pre-treatment data set and patient-specific objective post-treatment data set; and
transmit updated patient-specific data to the predictive modeling module for re-ranking the model data sets; and
the predictive modeling module is configured to modify at least one of the first graphical image and the second graphical image.

10. The system of claim 1 wherein the treatment plan generator is further configured to receive actual patient-specific post-treatment data, and wherein the post-treatment data is generated at one or more time points following treatment.

11. The system of claim 10 wherein the patient-specific data includes pre-treatment data, and wherein the pre-treatment data, the actual patient-specific post-treatment data, and the best-fit combination of treatment parameters are deposited in the database as a new model data set.

12. The system of claim 11 wherein:
the patient-specific treatment plan is a first patient-specific treatment plan provided for a patient; and
the treatment plan generator is further configured to—
rank the plurality of model data sets in accordance with a degree of affinity to patient-specific pre-treatment data; and
positively weigh the new model data set when ranking the plurality of model data sets for generating a second patient-specific treatment plan for the patient.

13. The system of claim 1 wherein the patient-specific data includes one or more image files corresponding to the patient's target region to be treated, and wherein the treatment plan generator is configured to extract target region data from the image files to compare to the plurality of model data sets in the database.

14. The system of claim 1 wherein the treatment plan generator is configured to query the client computer for additional patient-specific data.

15. The system of claim 1 wherein the treatment plan generator assigns a unique identification number to a patient-specific pre-treatment data set.

16. The system of claim 1 wherein the treatment plan generator resides on a server connected to the computer network.

17. The system of claim 1 wherein the treatment plan generator resides on the client computer.

18. A system for developing and administering a patient-specific treatment plan comprising:
a computing device;
a user interface in communication with the computing device for enabling a user to request a treatment plan and to specify patient-specific data, wherein patient-specific data includes at least one of a target region pre-treatment data element and an objective post-treatment data element;
a predictive modeling module configured to—
receive and compare the patient-specific data to a plurality model data sets, wherein the model data sets comprise at least one of empirically-derived data and a priori information, and wherein the model data sets correspond to unique combinations of treatment parameters; and
rank the plurality of model data sets in accordance with a degree of affinity to the patient-specific data;
a treatment plan formulation module configured to automatically calculate a best-fit combination of treatment parameters from a plurality of treatment parameters to generate the patient-specific treatment plan for non-invasively transdermally removing heat from subcutaneous lipid-rich cells in a target region contour of a patient, wherein calculating the best-fit combination includes determining the unique combination of treatment parameters corresponding to one or more model data sets having a highest affinity to the patient-specific data; and
a treatment system in communication with the computing device for non-invasive, transdermal heat removal from the lipid-rich cells in the target region contour, the treatment system configured to receive the patient-specific treatment plan from the treatment formulation module, and administer treatment to the lipid-rich target region, wherein the treatment includes the best-fit combination of treatment parameters.

19. The system of claim 18 wherein the predictive modeling module is further configured to:
generate and transmit to the user interface a first graphical image representing the model data set having a highest degree of affinity to the patient-specific data; and
determine an anticipated feedback data set based on the one or more model data sets having a highest affinity to the patient-specific data and the best-fit combination treatment parameters, wherein the anticipated feedback data includes one or more heat flux measurements.

20. The system of claim 19, further comprising a real-time optimization module configured to:
receive real-time feedback data during treatment administration from the computing device;
compare real-time feedback data to the anticipated feedback data set;
calculate a difference between the real-time feedback data and the anticipated feedback data;
modify the best-fit combination of treatment parameters to generate a modified treatment plan; and
transmit the modified treatment plan to the treatment system for changing treatment administration in real-time.

21. The system of claim 18 wherein the treatment system includes:
a treatment device having an applicator and one or more heat exchanging units; and
a controller for modifying operation of the treatment device upon receiving treatment plan instructions and modified treatment plan instructions, wherein the controller is in communication with the computing device.

22. The system of claim 21 wherein the treatment parameters include cooling temperature and duration profiles for the one or more heat exchanging units.

23. The system of claim 18 wherein:
the patient-specific data comprises one or more objective post-treatment data elements;
the system further comprises a real-time optimization module configured to—
receive real-time feedback data during preliminary treatment administration from the computing device to determine actual target region data; and
deliver the patient-specific treatment plan to the computing device in real-time;
the predictive modeling module is configured to receive and compare the actual target region data to the plurality model data sets, and rank the plurality of model data sets in accordance with a degree of affinity to the actual target region data and the objective post-treatment data elements;
the treatment plan formulation module is configured to calculate the best-fit combination of treatment parameters to generate the patient-specific treatment plan, wherein calculating the best-fit combination includes determining the unique combination of treatment parameters corresponding to one or more model data sets having a highest affinity to the actual target region data and the objective post-treatment data elements; and
the treatment system is configured to receive the patient-specific treatment plan from the computing device in real-time and modify treatment parameters during treatment based on the patient-specific treatment plan.

24. The system of claim 18 wherein the patient data comprises one or more target region pre-treatment data elements, and wherein the predictive modeling module is configured to generate a first graphical image representing the target region pre-treatment data elements and generate a second graphical image representing a recommended post-treatment outcome.

25. The system of claim 18, further comprising a position sensor in communication with the computing device, the position sensor configured to detect and transmit data relating to the position and size of the lipid-rich target region relative to a reference point.

26. The system of claim 18, further comprising a medical imaging device for generating one or more images defining one or more aspects of the lipid-rich target region.

27. The system of claim 18 wherein at least one of the predictive modeling module and the treatment plan formulation module resides on a server in communication with the computing device.

28. The system of claim 18 wherein at least one of the predictive modeling module and the treatment plan formulation module reside on the computing device.

29. A system for developing and administering a patient-specific treatment plan comprising:
a treatment system for non-invasive, transdermal removal of heat from subcutaneous lipid-rich cell of a patient;
a computing device in communication with the treatment system and configured to receive and transmit patient-specific data and patient-specific treatment plans, wherein the patient-specific data includes one or more objective post-treatment data elements and real-time feedback data;
a treatment plan generator in communication with the computing device and configured to receive and compare the patient-specific data to a plurality of model data sets, wherein the model data sets correspond to unique combinations of treatment parameters, and wherein the treatment plan generator includes—
a real-time optimization module configured to receive real-time feedback data from the computing device during preliminary treatment administration to determine actual target region data;
a predictive modeling module configured to receive and compare the actual target region data to the plurality model data sets, and rank the plurality of model data sets in accordance with a degree of affinity to the actual target region data and the one or more objective post-treatment data elements; and
a treatment plan formulation module configured to calculate a best-fit combination of treatment parameters to generate the patient-specific treatment plan, wherein calculating the best-fit combination includes determining the unique combination of treatment parameters corresponding to one or more model data sets having a highest affinity to the actual target region data and the one or more objective post-treatment data elements; and
wherein the treatment system is configured to receive the patient-specific treatment plan from the computing device in real-time and modify treatment parameters during treatment based on the patient-specific treatment plan.

30. The system of claim 29 wherein the real-time feedback data includes one or more heat flux measurements, and wherein the one or more heat flux measurements is used to determine a subcutaneous adipose tissue thickness.

31. The system of claim 29 wherein the treatment system includes a treatment device having an applicator and one or more heat exchanging units, and wherein the treatment parameters include cooling temperature and duration profiles for the one or more heat exchanging units.

32. A non-transitory computer-readable medium whose contents cause at least one computer to perform a method for generating a patient-specific treatment plan, the method comprising:
receiving patient-specific data and a request for generating a patient-specific treatment plan, wherein the patient-specific data relates to a current body contour at a lipid-rich target region of a patient and includes real-time feedback data, and wherein the patient-specific treatment plan includes operational parameters for administering treatment to the patient for altering the current body contour;
creating a pre-treatment data set comprising lipid-rich target region data elements;
comparing the pre-treatment data set to a plurality of model data sets, wherein the model data sets correspond to unique combinations of treatment parameters;
ranking the plurality of model data sets in accordance with a degree of affinity to the pre-treatment data set;
calculating a best-fit combination of treatment parameters from the unique combination of treatment parameters corresponding to one or more model data sets having a highest affinity to the pre-treatment data set; and
generating, in real-time, the patient-specific treatment plan for implementation by a treatment system, wherein the patient-specific treatment plan includes the best-fit combination of treatment parameters.

33. The computer-readable medium of claim 32, further comprising:
receiving real-time feedback data during treatment administration, wherein the real-time feedback data includes a heat flux measurement;

comparing real-time feedback data to an anticipated feedback data set;
calculating a difference between the real-time feedback data and the anticipated feedback data set to create a patient-specific actual data set; and
modifying the best-fit combination of treatment parameters to generate a modified treatment plan based on at least the patient-specific actual data set.

34. The computer-readable medium of claim 32 wherein the treatment plan includes a treatment plan for non-invasive, transdermal removal of heat from subcutaneous lipid-rich cells of a patient, and wherein receiving patient-specific data includes receiving data relating to at least one of a target region body position and a subcutaneous adipose tissue thickness.

35. The computer-readable medium of claim 34 wherein:
receiving data relating to at least one of target region body position and a subcutaneous adipose tissue thickness includes receiving data relating to an estimated subcutaneous adipose tissue thickness;
the treatment plan is generated based at least in part on the estimated thickness; and
wherein the method further comprises—
receiving real-time feedback data during treatment administration, wherein the real-time feedback data includes an actual subcutaneous adipose tissue thickness measurement; and
modifying the best-fit combination of treatment parameters to generate a modified treatment plan based on the actual thickness measurement.

36. The computer-readable medium of claim 32, further comprising:
displaying a first graphical image, wherein the first graphical image represents the current body contour; and
displaying a second graphical image, wherein the second graphical image represents a predicted post-treatment body contour.

37. The computer-readable medium of claim 32 wherein receiving patient-specific data includes receiving target region pre-treatment data and objective post-treatment data, and wherein ranking the plurality of model data sets includes ranking in accordance with a degree of affinity to the target region pre-treatment data and the objective post-treatment data.

38. The computer-readable medium of claim 32 wherein the treatment plan includes a treatment plan for non-invasive, transdermal ablation of subcutaneous lipid-rich cells of a patient using high intensity focused ultrasound energy.

39. A non-transitory computer-readable medium whose contents cause at least one computer to perform a method for providing a treatment plan for altering a patient body contour, the method comprising:
receiving patient-specific objective post-treatment data relating to a desired body contour;
receiving actual patient-specific data relating to a current body contour generated during preliminary treatment administration;
ranking a plurality of model data sets in accordance with a degree of affinity to the actual patient-specific data and the patient-specific objective post-treatment data, wherein the model data sets include at least one of empirically-derived data and a priori information, and wherein the model data sets correspond to unique combinations of treatment parameters;
automatically calculating a best-fit combination of treatment parameters from the unique combination of treatment parameters corresponding to one or more model data sets having a highest affinity to the actual patient-specific data and the patient-specific objective post-treatment data; and
providing a treatment plan for administering treatment to alter the current body contour to a body contour at least approximate to the desired body contour, wherein the treatment plan includes the best-fit combination of treatment parameters.

40. The computer-readable medium of claim 39 wherein the treatment parameters include cooling temperature and duration profiles for one or more heat exchanging units applied to a skin of a patient.

41. The computer-readable medium of claim 39 wherein receiving actual patient-specific data relating to a current body contour includes receiving the actual patient-specific data in real-time, and wherein providing a treatment plan for administering treatment includes providing the treatment plan for administering treatment in real time.

42. The computer-readable medium of claim 39, further comprising:
displaying a first graphical image, wherein the first graphical image represents the actual patient-specific data; and
displaying a second graphical image, wherein the second graphical image represents an anticipated post-treatment result, and wherein the anticipated post-treatment result is based on the actual patient-specific data and the patient-specific objective post-treatment data.

43. The computer-readable medium of claim 39 wherein receiving actual patient-specific data relating to a current body contour includes receiving one or more heat flux measurements, and wherein the heat flux measurements are used to determine a subcutaneous adipose tissue thickness.

44. A non-transitory computer-readable medium whose contents cause at least one computer to perform a method for providing a user interface relating to generating a treatment plan for cooling a subcutaneous lipid-rich target region of a patient, the method comprising:
receiving patient-specific data relating to the subcutaneous lipid-rich target region;
displaying a first graphical image representing the patient-specific data;
automatically generating a treatment plan including a calculated best-fit combination of treatment parameters for achieving a desired treatment result
receiving objective post-treatment data relating to the desired treatment result; and
displaying a second graphical image representing the desired treatment result, wherein the second graphical image is based upon the patient-specific data and the objective post-treatment data.

45. The computer-readable medium method of claim 44 wherein the method further comprises displaying the treatment plan.

46. The computer-readable medium of claim 44, wherein the method further comprises receiving additional patient-specific data for modifying at least the second graphical image.

* * * * *